US009005895B2

(12) United States Patent
Woo et al.

(10) Patent No.: US 9,005,895 B2
(45) Date of Patent: Apr. 14, 2015

(54) COMPOSITIONS, METHODS AND KITS FOR NUCLEIC ACID SYNTHESIS AND AMPLIFICATION

(75) Inventors: Cora L. Woo, Santa Clara, CA (US); Jennifer Berkman, San Francisco, CA (US); Priscilla W. Yim, San Mateo, CA (US)

(73) Assignee: Life Technologies Corporation, Carlsbad, CA (US)

( * ) Notice: Subject to any disclaimer, the term of this patent is extended or adjusted under 35 U.S.C. 154(b) by 231 days.

(21) Appl. No.: 13/164,177

(22) Filed: Jun. 20, 2011

(65) Prior Publication Data

US 2012/0003645 A1 Jan. 5, 2012

Related U.S. Application Data

(60) Provisional application No. 61/357,021, filed on Jun. 21, 2010, provisional application No. 61/467,852, filed on Mar. 25, 2011.

(51) Int. Cl.
*C12Q 1/68* (2006.01)
*C12P 19/34* (2006.01)

(52) U.S. Cl.
CPC .................................. *C12Q 1/6848* (2013.01)

(58) Field of Classification Search
None
See application file for complete search history.

(56) References Cited

U.S. PATENT DOCUMENTS

| | | | |
|---|---|---|---|
| 4,889,818 A | 12/1989 | Gelfand et al. | |
| 4,943,531 A | 7/1990 | Goff et al. | |
| 4,965,188 A | 10/1990 | Mullis et al. | |
| 5,017,492 A | 5/1991 | Kotewicz et al. | |
| 5,244,797 A | 9/1993 | Kotewicz et al. | |
| 5,374,553 A | 12/1994 | Gelfand et al. | |
| 5,455,170 A | 10/1995 | Abramson et al. | |
| 5,466,591 A | 11/1995 | Abramson et al. | |
| 5,538,848 A | 7/1996 | Livak et al. | |
| 5,668,005 A | 9/1997 | Kotewicz et al. | |
| 5,912,155 A | 6/1999 | Chatterjee et al. | |
| 5,925,517 A | 7/1999 | Tyagi et al. | |
| 6,103,476 A | 8/2000 | Tyagi et al. | |
| 6,150,097 A | 11/2000 | Tyagi et al. | |
| 6,168,918 B1 * | 1/2001 | Satishchandran et al. | 435/6.12 |
| 6,200,757 B1 | 3/2001 | Kurn et al. | |
| 6,210,882 B1 | 4/2001 | Landers et al. | |
| 6,303,305 B1 | 10/2001 | Wittwer et al. | |
| 6,355,421 B1 | 3/2002 | Coull et al. | |
| 6,383,752 B1 | 5/2002 | Agrawal et al. | |
| 6,403,341 B1 | 6/2002 | Barnes et al. | |
| 6,485,901 B1 | 11/2002 | Gildea et al. | |
| 6,503,720 B2 | 1/2003 | Wittwer et al. | |
| 6,548,250 B1 | 4/2003 | Sorge | |
| 6,589,250 B2 | 7/2003 | Schendel | |
| 6,589,743 B2 | 7/2003 | Sorge et al. | |
| 6,590,091 B2 | 7/2003 | Albagli et al. | |
| 6,593,091 B2 | 7/2003 | Keys et al. | |
| 6,596,490 B2 | 7/2003 | Dattagupta | |
| 6,727,356 B1 | 4/2004 | Reed et al. | |
| 6,783,934 B1 | 8/2004 | McMillan et al. | |
| 7,056,716 B2 | 6/2006 | Potter | |
| 7,078,208 B2 | 7/2006 | Smith et al. | |
| 7,228,237 B2 | 6/2007 | Woo et al. | |
| 2004/0096819 A1 | 5/2004 | McMillan | |
| 2004/0219595 A1 | 11/2004 | Lee et al. | |
| 2009/0197254 A1 | 8/2009 | Lee | |
| 2009/0269766 A1 | 10/2009 | Heindl | |

FOREIGN PATENT DOCUMENTS

| | | |
|---|---|---|
| WO | WO-92/06200 | 4/1992 |
| WO | WO-96/10640 | 4/1996 |
| WO | WO-98/47912 | 10/1998 |
| WO | WO-99/21881 | 5/1999 |
| WO | 2008/144556 | 11/2008 |
| WO | 2008/155524 | 12/2008 |
| WO | WO2011/163120 | 12/2011 |

OTHER PUBLICATIONS

Knecht et al.., "Decreased glutamate transporter (GLT-1) expression in frontal cortex of rats with acute liver failure," Neuroscience Letters, 1997, vol. 229, pp. 201-203.*
Shin et al., "Detection of cancer cells in peripheral blood of stomach cancer patients using RT-PCR amplification of tumor-specific mRNA," Aliment Pharmacol. Ther., 2002, vol. 16, pp. 137-144.*
Qiagen Product Description, "Qiagen OneStep RT-PCR Kit," [retrieved on-line: http://www.qiagen.com/products/catalog].*
Current Protocols in Molecular Biology, 2009, Chapter 15, 15.0.1-15.1.14.*
Yap et al., "Slide PCR: DNA amplification from cell samples on microscopic glass slides," Nucleic Acids Research, 1991, vol. 19, No. 15, p. 4294.*
Qiagen Product Description, "Qiagen OneStep RT-PCR Kit", [retrieved on-line: http://www.qiagen.com/products/catalog; retrieval date Mar. 2013].*
Al-Soud, W.A. et al., "Effects of amplification facilitators on diagnostic PCR in the presence of blood, feces, and meat", *Journal of Clinical Microbiology, American Society for Microbiology*, Washington, DC, vol. 38, No. 12, Jan. 1, 2000, pp. 4463-4470.
Jung, Roman et al., "Reversal of RT-PCR Inhibition Observed in Heparinized Clinical Specimens", *BioTechniques*, vol. 23, No. 1, Jul. 1997, pp. 24-28.
Nagai, M. et al., "Additive Effects of Bovine Serum Albumin, Dithiothreitol, and Glycerol on PCR", *Biochemistry and Molecular Biology International, Academic Press*, London, GB, vol. 44, No. 1, Jan. 1, 1998, pp. 157-163.
International Search Report and The Written Opinion of the International Searching Authority for Application No. PCT/US2011/041061 dated Sep. 1, 2011.

(Continued)

Primary Examiner — Young J Kim

(57) ABSTRACT

The present invention is directed to compositions, methods and kits useful for the synthesis of nucleic acid molecules. More specifically, compositions, methods and kits are provided for the amplification of nucleic acid molecules in a one-step RT-PCR procedure comprising one or more agents used to increase tolerance to PCR inhibitors.

24 Claims, 14 Drawing Sheets

(56) References Cited

OTHER PUBLICATIONS

U.S. Appl. No. 08/689,807 Specification.
U.S. Appl. No. 08/689,818 Specification.
Bej, Asim K. et al. "Thermostable DNA Polymerases for In Vitro DNA Amplifications", *In PCR Technology Current Innovations*, Chapter 25, H.G. Griffin and A.M. Griffin, Eds., CRC Press, 1994, 219-237.
Broude et al. "Stem-loop oligonucleotides: a robust tool for molecular biology and biotechnology", *Trends in Biotechnology*, vol. 20, No. 6, Jun. 2002, 249-256.
Chiou, J. et al. "A Closed-Cycle Capillary Polymerase Chain Reaction Machine", *Analytical Chemistry, American Chemical Society*, vol. 73, No. 9, 2001, 2018-2021.
Flaman, Jean-Michel et al. "A Rapid PCR Fidelity Assay", *Nucleic Acids Research*, vol. 22, No. 15, 1994, 3259-3260.
Gerard, Gary F. et al. "cDNA Synthesis by Moloney Murine Leukemia Virus RNase H-Minus Reverse Transcriptase Possessing Full DNA Polymerase Activity", *Focus*, vol. 14, No. 3, 1992, 91-93.
Giordano et al. "Polymerase Chain Reaction in Polymeric Microchips: DNA Amplification in Less Than 240 Seconds", *Analytical Biochemistry*, vol. 291, 2001, 124-132.
Gu et al. "Multiplexed, Real-Time PCR for Quantitative Detection of Human Adenovirus", *Journal of Clinical Microbiology*, vol. 41, No. 10, 2003, 4636-4641.
Huang et al. "Fluorescence Characteristics of Site-Specific and Stereochemically Distinct Benzo[a]pyrene Diol Epoxide-DNA Adducts as Probes of Adduct Conformation", *Chemical Research in Toxicology*, vol. 15, Issue 2, Feb. 2002, 118-126.
Isacsson et al. "Rapid and specific detection of PCR products using light-up probes", *Molecular Cell Probes*, vol. 14, 2000, 321-328.
Jothikuma, Narayanan et al. "Quantitative Real-Time PCR Assays for Detection of Human Adenoviruses and Identification of Serotypes 40 and 41", *Applied and Environmental Microbiology*, vol. 71, No. 6, 2005, 3131-3136.
Kalinina, Olga et al. "Nanoliter Scale PCR with TaqMan Detection", *Nucleic Acids Research*, vol. 25, No. 10, 1997, 1999-2004.
Kopp, Martin et al. "Chemical Amplification: Continuous-Flow PCR on a Chip", *Science*, vol. 280, 1998, 1046-1048.
Kotewicz et al. "Isolation of cloned Moloney murine leukemia virus reverse transcriptase lacking ribonuclease H activity", *Nucleic Acids Research*, vol. 16, No. 1, 1988, 265-277.
Kubista et al. "Light-up probe based real-time Q-PCR", *SPIE*, vol. 4264, 2001, 53-58.
Maxwell et al. "Self-Assembled Nanoparticle Probes for Recognition and Detection of Biomolecules", *Journal of the American Chemical Society*, vol. 124, Issue 32, Aug. 14, 2002, 9606-9612.
Mhlanga et al. "Using Molecular Beacons to Detect Single-Nucleotide Polymorphisms with Real-Time PCR", *Methods*, vol. 25, 2001, 463-471.
Myers, Thomas W. et al. "Reverse Transcription and DNA Amplification by a *Thermus thermophilus* DNA Polymerase", *Biochemistry*, vol. 30, No. 31, American Chemical Society, 1991, 7661-7666.
Noble, Rachel T. et al. "Multitiered Approach Using Quantitative PCR to Track Sources of Fecal Pollution Affecting Santa Monica Bay, Calif.", *Applied and Environmental Microbiology*, vol. 72, No. 2, 2006, 1604-1612.
Perbal, Bernard "A Practical Guide to Molecular Cloning", *A Wiley-Interscience Publication*, John Wiley & Sons, 1984, pp. 23-24.
Riccelli, et al. "Melting studies of dangling-ended DNA hairpins: effects of end length, loop sequence and biotynylationof loop bases", *Nucleic Acids Research* vol. 30, No. 18, Sep. 15, 2002, 4088-4093.
Sellner et al. "Reverse transcripts inhibits Taq polymerase activity", *Nucleic Acids Research*, vol. 20, No. 7, 1992, 1487-1490.
Sellner et al. "Simultaneous Synthesis of Partially Homologous Oligonucleotide Sequences", *BioTechniques*, vol. 25, 1998, 234-238.
Solinas et al. "Duplex Scorpion primers in SNP analysis and FRET applications", *Nucleic Acids Research*, vol. 29, No. 20, Oct. 15, 2001, E96: pp. 1-9.
Svanvik et al. "Light-Up Probes: Thiazole Orange-Conjugated Peptide Nucleic Acid for Detection of Target Nucleic Acid in Homogeneous Solution", *Analytical Biochemistry*, vol. 281, 2000, 26-35.
Tsourkas et al. "Structure-function relationships of shared-stem and conventional molecular beacons", *Nucleic Acids Research*, vol. 30, No. 19, Oct. 1, 2002, 4208-4215.
Tyagi, Sanjay et al. "Molecular Beacons: Probes that Fluoresce upon Hybridization", *Nature Biotechnology*, vol. 14, Mar. 1996, 303-308.
Villa, Luisa L. et al. "Methods for Detection of HPV Infection and its Clinical Utility", *International Journal of Gynecology & Obstetrics*, vol. 94 (Supplemental 1), 2006, S71-S80.
Whitcombe, David et al. "Detection of PCR products using self-probing amplicons and fluorescence", *Nature Biotechnology*, vol. 17, Aug. 1999, 804-807.
Wolffs et al. "PNA-Based Light-Up Probes for Real-Time Detection of Sequence-Specific PCR Products", *BioTechniques*, vol. 31, No. 4, Oct. 2001, 766-771.
Yu et al. "Electronic Detection of Single-Base Mismatches in DNA with Ferrocene-Modified Probes", *Journal of the American Chemical Society*, vol. 123, Issue 45, Nov. 14, 2001, 11155-11161.
Zhang et al. "Hairpin Probes for Real-time Assay of Restriction Endonucleases", *Shanghai*, vol. 34, 2002, 329-332.
Akane, et al., "Identification of the Heme Compound Copurified with Deoxyribonucleic Acid (DNA) from Bloodstains, a Major Inhibitor of Polymerase Chain Reaction (PCR) Amplification", *Journal of Forensic Sciences*, vol. 39, No. 2, American Academy of Forensic Sciences, Mar. 1994, pp. 362-372.
Back, et al., "Increased Thermal Stability of Proteins in the Presence of Sugars and Polyols", *Biochemistry*, vol. 18, No. 23, Back Oakenfull and Smith, 1979, pp. 5191-5196.
Forbes, et al., "Substances Interfering with Direction Detection of *Mycobacterium tuberculosis* in Clinical Specimens by PCR: Effects of Bovine Serum Albumin", *Journal of Clinical Microbiology*, vol. 34, No. 9, Sep. 1996, pp. 2125-2128.
Gekko, et al., "Thermodynamic and Kinetic Examination of Protein Stabilization by Glycerol", *Biochemistry*, vol. 20, 1981, pp. 4677-4686.
Jordan, et al., "Activity and Dimerization of Human Immunodeficiency Virus Protease as a Function of Solvent Composition and Enzyme Concentration", *The Journal of Biological Chemistry*, vol. 267, No. 28, The American Society for Biochemistry and Molecular Biology, Inc., Oct. 5, 1992, pp. 20028-20032.
Lin, et al., "Sex determination by polymerase chain reaction on mummies discovered in Taklamakan desert in 1912", *Forensic Science International*, vol. 75, 1995, pp. 197-205.
McGregor, et al., "Simultaneous Detection of Microorganisms in Soil Suspension Based on PCR Amplification of Bacterial 16S rRNA Fragments", *BioTechniques*, vol. 21, No. 3, Sep. 1996, pp. 463-471.
Nikol'Skaya, et al., "Factors of Activation and Stabilization of DNA-Methylases From *Shigella sonnei* 47 and *Mycobacterium smegmatis* Butyricum Cells", *Biochemistry International*, vol. 15, No. 1, Jul. 1987, pp. 127-138.
Wong, et al., "Branch capture reactions: displacers derived from asymmetric PCR", *Nucleic Acids Research*, vol. 19, No. 9, 1991, pp. 2251-2259.
U.S. Appl. No. 08/689,807 Specification, filed Aug. 1996.
U.S. Appl. No. 08/689,818 Specification, filed Aug. 1996.
Opel et al., "A Study of PCR Inhibition Mechanisms Using Real Time PCR", *Journal Forensic Sciences*, vol. 55, No. 1, Jan. 1, 2010, 25-33.
Al-Soud et al., "Identification and Characterization of Immunoglobulin G in Blood as a Major Inhibitor of Diagnostic PCR", *Journal of Clinical Microbiology*, vol. 38, No. 1, Jan. 2000, 345-350.
Al-Soud et al., "Purification and Characterization of PCR-Inhibitory Components in Blood Cells", *Journal of Clinical Microbiology*, vol. 39, No. 2, Feb. 2001, 485-493.
Bickley et al., "Chapter 6: Inhibitors and Enhancers of PCR", *Analytical Molecular Biology: Quality and Validation*, vol. 8, 1999, 81-102.

(56) References Cited

OTHER PUBLICATIONS

Bu et al., "Direct Polymerase Chain Reaction (PCR) from Human Whole Blood and Filter-Paper-Dried Blood by Using a PCR Buffer with a Higher pH", *Analytical Biochemistry*, vol. 375, Jan. 12, 2008, 370-372.

Drugs.Com, "Heparin (Systemic)", www.drugs.com/mmx/herapin, Aug. 23, 1994, 1-25.

Garcia et al., "Anticoagulants Intefere with PCR Used to Diagnose Invasive Aspergillosis", *Journal of Clinical Microbiology*, vol. 40, No. 4, Apr. 2002, 1567-1568.

Kermekchiev et al., "Mutants of Taq DNA polymerase resistant to PCR inhibitors allow DNA amplification from whole blood and crude soil samples", *Nucleic Acids Reseaerch*, vol. 37, No. 5, Feb. 10, 2009, e40 (1-14).

Radstrom et al., "Pre-PCR Processing of Samples", *Methods in Molecular Biology*, vol. 216, Nov. 14, 2002, 31-50.

Radstrom et al., "Topic Introduction: Strategies for Overcoming PCR Inhibition", *Cold Spring Harbor Protocols*, eds. Dieffenbach and Dveksler, NY, US, 2003, 1-9.

\* cited by examiner

Fish gelatin and BSA enable the successful amplification, and subsequent detection of amplification products by gel electrophoresis of samples containing various inhibitors

COMPOSITIONS, METHODS AND KITS FOR NUCLEIC ACID SYNTHESIS AND AMPLIFICATION

CROSS-REFERENCE TO RELATED APPLICATIONS

This application claims the benefit of priority under 35 U.S.C. §119(e) to U.S. Provisional Patent Application Nos. 61/357,021, filed Jun. 21, 2010 and 61/467,852, filed Mar. 25, 2011, which are herein incorporated by reference in their entirety.

FIELD

The disclosure relates to compositions, methods and kits useful for the synthesis of nucleic acids. More specifically, compositions, methods and kits are provided for the amplification of nucleic acid molecules in a one-step RT-PCR procedure comprising one or more agents used to increase tolerance to PCR inhibitors.

BACKGROUND

The detection, analysis, transcription, and amplification of nucleic acids are some of the most important procedures in modern molecular biology. The application of such procedures for nucleic acid analysis is especially important in the investigation of gene expression, diagnosis of infectious agents or genetic diseases, the generation of cDNA, and analysis of retroviruses, to name but a few applications. The reverse transcription of RNA, followed by polymerase chain reaction (PCR) cDNA amplification, commonly referred to as RT-PCR or RNA-PCR, has become widely used for the detection and quantification of nucleic acid targets and is particularly important for viral gene analysis.

The study of oncoviruses and their roles in the pathogenesis of carcinomas can have important implications in the diagnosis and treatment of cancer. However, variability in the detection of oncoviruses can make these studies challenging. Sensitivity and specificity of the detection method are key concerns. Earlier detection can be achieved using molecular biology techniques to detect oncoviral nucleic acids in samples that have not undergone seroconversion, and these techniques are applicable to viruses that cannot be propagated in tissue culture. Traditionally, immunological detection methods have been used to detect the presence of oncoviruses, but these methods have several drawbacks. In the case of Human Papillomavirus (HPV), which can cause cervical cancer, detection is difficult due to low expression of early viral proteins and a lack of sensitive and specific high-quality antibodies that can discriminate HPV types (Villa and Denny, *International Journal of Gynecology and Obstetrics*, 94(Suppl. 1):S71-S80 (2006)). Results can also be misleading or inconclusive when a sample exhibits residual antibody levels due to an infection that may have happened months or years prior to sample collection, as in the case of the Epstein-Barr Virus (EBV), which is associated with Hodgkin's lymphoma and other carcinomas (National Center for Infectious Diseases. "Epstein-Barr Virus and Infectious Mononucleosis," CDC. www.cdc.gov/ncidod/diseases/ebv (November 2010)). PCR-based detection of viral nucleic acids not only has the advantage of being highly specific due to sequence specific primer binding, it is also less cumbersome and more sensitive than other hybridization techniques, such as the Northern and Southern blots, due to its ability to amplify shorter nucleic acid fragments. Sequence-specific probe binding adds an additional layer of specificity to real-time PCR and has the additional advantage of providing viral load information.

RT-PCR typically involves two separate molecular syntheses: (i) the synthesis of cDNA from an RNA template; and (ii) the replication of newly synthesized cDNA through PCR amplification. RT-PCR can be performed by one-step (or coupled) RT-PCR methods using two or more enzymes, in which at least two separate enzymes (e.g., a reverse transcriptase and a polymerase) are employed for initial cDNA synthesis and subsequent amplification, respectively.

In one-step RT-PCR, reverse transcription and PCR amplification are combined into a single reaction mixture which provides numerous advantages over two-step RT-PCR (where the synthesis and amplification steps are performed using two different or separate reactions). One-step RT-PCR requires less handling of the reaction mixture reagents and nucleic acid products than two-step RT-PCR (e.g., opening of the reaction tube for component or enzyme addition in between the two reaction steps), and is therefore less labor intensive and time consuming. One-step RT-PCR also allows for less sample to be used if necessary, and reduces the risk of contamination (Sellner and Turbett, *Biotechniques* 25:234-238 (1998)).

The use of one-step RT-PCR methods have some drawbacks, however. For example, individual optimization of the ratio of reverse transcriptase to DNA polymerase is usually not practicable for ready-to-use compositions or kits for one-step RT-PCR. Several reports have also documented interference between reverse transcriptase and DNA polymerase when used in combination in a single tube RT-PCR reaction resulting in low sensitivity or lack of results (Sellner, L. N., et al., *Nucl. Acids Res.* 20:1487-1490 (1992)).

Moreover, samples from which viral nucleic acids are extracted often contain additional compounds that are inhibitory to PCR. Humic acid in soil and feces, hematin in blood, immunoglobin G in serum, and various blood anticoagulants, like heparin and citrate, are all examples of such inhibitors. Such inhibitors may not be completely removed during the nucleic acid extraction and purification process, thus negatively impacting downstream PCR amplification, as reflected by an increase in $C_t$ (i.e., threshold cycle) and decrease in dRn (i.e., difference in normalized reporter signal) when assayed by real time PCR.

A high $C_t$ coupled with low dRn usually indicates low target nucleic acid concentration in reactions for quantitative PCR (qPCR) and reverse transcriptase-qPCR (RT-qPCR) applications. A reaction that exhibits reduced or no amplification indicates that the target nucleic acid is absent, or present in such small amounts that it is not detectable. A reaction that contains detectable amounts of target, but is inhibited by the presence of PCR inhibitors may show an artificially high $C_t$ and low dRn, which can lead the user to believe that the amount of target nucleic acid is less than the actual amount present. If the level of inhibition is severe enough, the reaction may fail to amplify completely, thus leading to a false-negative result.

Because of the importance of nucleic acid synthesis applications to the fields of molecular biology and cellular biology, a one-step RT-PCR system, in the form of a generalized ready-to-use composition, which exhibits high sensitivity, is not restricted by the amount of sample, reduces the amount of practitioner manipulation, minimizes the risks of contamination, minimizes the expense of reagents, and maximizes the amount of nucleic acid end product, is needed in the art. In addition, a method to reduce or eliminate the negative effects of PCR inhibitors, especially when analyzing viral targets where sample sources often contain such inhibitors, is necessary to ensure accurate results.

SUMMARY

The present invention is generally directed to compositions, methods and kits useful for the synthesis of nucleic acids. More specifically, compositions, methods and kits are provided for the amplification of nucleic acid molecules in a one-step RT-PCR procedure using one or more reverse transcriptases, such as Moloney Murine Leukemia Virus (M-MLV) reverse transcriptase, in combination with one or more DNA polymerases, such as DNA polymerase from *Thermophilus aquaticus* (Taq). Preferably, the compositions further comprise one or more agents used to increase tolerance to (i.e., block or alleviate PCR inhibition) by a variety of compounds often found in samples from which nucleic acids, especially viral nucleic acids, are extracted (e.g., feces, blood, soil, etc.). Such PCR inhibitor blocking agents can include, for example, bovine serum albumin (BSA) and fish gelatin. The present teachings thus facilitate the rapid and efficient amplification of nucleic acid molecules and the detection and quantitation of target sequences which can be used for a variety of industrial, medical, forensic and diagnostic purposes. The embodiments disclosed herein are especially useful for the rapid amplification and detection of viral genes, including both RNA and DNA targets.

In particular, the present teachings are directed to compositions comprising at least one active DNA polymerase and at least one active reverse transcriptase (RT). In some embodiments, such compositions further comprise at least one PCR inhibitor blocking agent, wherein said PCR inhibitor blocking agents increase tolerance to one or more PCR inhibitors, if present.

In some embodiments, the reverse transcriptases of the present compositions are reverse transcriptases. In some preferred embodiments the reverse transcriptases are thermostable. For instance, the thermostable reverse transcriptases can be M-MLV reverse transcriptases, mutants, variants, or derivatives thereof. In some embodiments, the M-MLV RTs can comprise one or more mutations. Such mutations can include, for example: Y64, R116, D124, H126, Y133, K152, Q190, T197, H204, V223, M289, T306, or F309. In some embodiments, the concentration of the reverse transcriptase(s) is between about 0.5 µU/µL to about 5 U/µL.

In some embodiments, the polymerases of the present compositions are DNA polymerases. In some preferred embodiments the DNA polymerases are thermostable DNA polymerases. For example, the thermostable DNA polymerases can be Taq DNA polymerases, mutants, variants, or derivatives thereof. In some embodiments, the concentration of the DNA polymerase(s) is between about 0.005 U/µL to about 0.5 U/µL.

In some embodiments, the PCR inhibitor blocking agents of the present compositions are proteins, polypeptides or peptide derivatives thereof. In some preferred embodiments the PCR inhibitor blocking agents can be gelatin, albumin or combinations thereof. These can include, for example, fish gelatin or bovine serum albumin (BSA). In some more preferred embodiments, the present compositions can comprise at least both fish gelatin and BSA. In some embodiments the concentration of BSA in the present compositions can be about 500 ng/µL to about 5000 ng/µL. In other embodiments, the final concentration of fish gelatin in the present compositions can be about 0.4% to about 4%.

In some embodiments, the PCR inhibitors, if present in the compositions, can be hematin, humic acid, heparin, EDTA, sodium citrate or Immunoglobulin G (IgG).

In some embodiments, the present compositions can be a liquid or gel at −20° C. In other embodiments the compositions may not be solid at about −20° C. In yet other embodiments the compositions may not be frozen at about −20° C. In some preferred embodiments the compositions do not require thawing prior to use.

In some embodiments, the present compositions can further comprise one or more nucleotides (dNTPs). Such nucleotides can be, for example, dTTP, dATP, dCTP, dGTP or dUTP. In some embodiments the concentration of each of the nucleotides in the composition is about 0.5 mM to about 5 mM.

In some embodiments, the present compositions can further comprise glycerol. In some embodiments the concentration of glycerol is between about 5% to about 50%.

In some embodiments of the present compositions, the compositions can further comprise RNase inhibitor protein (RIP). In some embodiments the concentration of RIP is between about 0.1 U/µL to about 1.0 U/µL.

In some embodiments, the present compositions can further comprise one or more detergents. In some embodiments the concentration of the one or more detergents is between about 0.005% to about 0.05%. In some embodiments the one or more detergents can be cationic, Zwitterionic, anioinic or non-ionic. In some embodiments, the non-ionic detergents can be, for example, Nonidet P-40 (NP-40) detergent or TWEEN 20 detergent.

In some embodiments, the present compositions can further comprise one or more passive reference control. In some embodiments, the one or more passive reference control can be, for example, a ROX dye.

In some embodiments, the present compositions can be formulated as concentrated stock solutions. In some embodiments, such concentrated stock solutions can be from about a 2× to about a 6× stock solution. In some embodiments, such stock solutions can be diluted for subsequent use in, for example, nucleic acid synthesis methods. In some preferred embodiments the compositions can be formulated as at least a 4× stock solution.

The present teachings are also directed to methods for performing RT-PCR of a nucleic acid sample. In some embodiments, the present methods can comprise the steps of: (i) mixing a composition comprising at least one reverse transcriptase, at least one DNA polymerase, or at least one PCR inhibitor blocking agent, wherein said PCR inhibitor blocking agent increases tolerance to one or more PCR inhibitors when present, with: (a) a nucleic acid sample; (b) one or more labeled probes; and (c) one or more primers; and (ii) performing RT-PCR on said nucleic acid sample.

In some embodiments of the present methods, the nucleic acid sample can be extracted from sources such as, for example, blood, sweat, tears, soil, saliva, urine, or feces.

In some embodiments of the present methods, RT-PCR can be performed in a single vessel (e.g., tube, compartment, well) or in a single reaction mixture.

In some embodiments of the present methods, compositions comprising at least one reverse transcriptase, at least one DNA polymerase, and at least one PCR inhibitor blocking agent are mixed with (a) a nucleic acid sample; (b) one or more labeled probes; or (c) one or more primers. In some embodiments of the present methods, the one or more labeled probes can be a TaqMan® probe. In some embodiments of the present methods, the compositions are not thawed prior to mixing with (a), (b), or (c).

In some embodiments of the present methods, the use of compositions comprising at least one PCR inhibitor blocking agent can increase tolerance to various PCR inhibitors (herein referred to as "inhibitor tolerance"), if present. In some embodiments, the increase in inhibitor tolerance can be indicated by a decrease in $C_t$. In some preferred embodiments of the present methods, $C_t$ is decreased by at least about 10% when compared to methods using compositions that do not comprise any PCR inhibitor blocking agents. In some embodiments, $C_t$ can be decreased by at least 1. In some embodiments, the use of compositions comprising at least 500 ng/μL BSA can decrease the $C_t$ by at least 8 for reactions containing at least 40 μM hematin, or by at least 7 for reactions containing at least 10 ng/μL humic acid. In other embodiments, the use of compositions comprising at least 1% fish gelatin can decrease the $C_t$ by at least 3 for reactions containing at least 10 ng/μL humic acid, or by at least 6 for reactions containing at least 0.06 U heparin.

In another aspect, the present teachings are directed to methods for amplifying a nucleic acid molecule. In some embodiments, the methods for amplification can comprise the steps of: (i) mixing a nucleic acid template with a composition comprising one or more reverse transcriptases, one or more DNA polymerases, and one or more PCR inhibitor blocking agents, to form a reaction mixture; and (ii) incubating the reaction mixture under conditions sufficient to amplify a nucleic acid molecule complementary to all or a portion of said nucleic acid template. In some embodiments, the nucleic acid template can be RNA or DNA.

In some embodiments of the present methods, nucleic acid amplification can be performed by PCR. In some embodiments, the PCR can be qPCR. In other embodiments, the qPCR can be performed by real time PCR. In other embodiments, the PCR can be endpoint PCR. In some other embodiments the PCR can be multiplex PCR. In yet other embodiments, the PCR can comprise thermal cycling. In some embodiments, the thermal cycling can be optimized for fast thermal cycling.

In another aspect, the present teachings are directed to methods for nucleic acid synthesis. In some embodiments the methods for nucleic acid synthesis can comprise: (i) mixing one or more first nucleic acid molecules with one or more reverse transcriptases, one or more polymerases, and one or more PCR inhibitor blocking agents; and (ii) incubating the mixture under conditions sufficient to make one or more second nucleic acid molecules complementary to all or a portion of one or more first nucleic acid molecules. In some embodiments, the first nucleic acid molecules are RNA molecules. In some embodiments, the first and second nucleic acid molecules are DNA molecules. In other embodiments, the first or second nucleic acid molecules are DNA molecules. In some embodiments, the methods for nucleic acid synthesis can further comprise incubating one or more first nucleic acid molecules under conditions sufficient to make one or more second nucleic acid molecules complementary to all or a portion of one or more first nucleic acid molecules.

The invention is also directed to reaction mixtures comprising: (a) at least one reverse transcriptase; (b) at least one polymerase; (c) at least one PCR inhibitor blocking agent; and (d) at least one primer. In some embodiments the reaction mixture can further comprise a nucleic acid template (e.g. RNA or DNA). In yet other embodiments, the reaction mixtures can further comprise a labeled probe (e.g., TaqMan® probe).

The invention is also directed to kits comprising, for example, in a single container, a composition having at least one reverse transcriptase, at least one DNA polymerase, and at least one PCR inhibitor blocking agent. In some embodiments, the composition can be housed in a single tube or vessel. In other embodiments, the composition can be a liquid or a gel (e.g. not solid or not frozen) at −20° C.

In some embodiments of the present kits, the compositions can be formulated as 4× stock solutions. In some preferred embodiments of the kits, the compositions can be used for RT-PCR methods, nucleic acid synthesis methods, or nucleic acid amplification (e.g., PCR) methods. In some embodiments, the PCR or RT-PCR methods can comprise multiplexing.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several exemplary embodiments of the disclosure and together with the description, serve to explain certain teachings. The skilled artisan will understand that the described drawings are for illustration purposes only. The drawings are not intended to limit the scope of the present teachings in any way.

DETAILED DESCRIPTION

Overview

Figure 1:
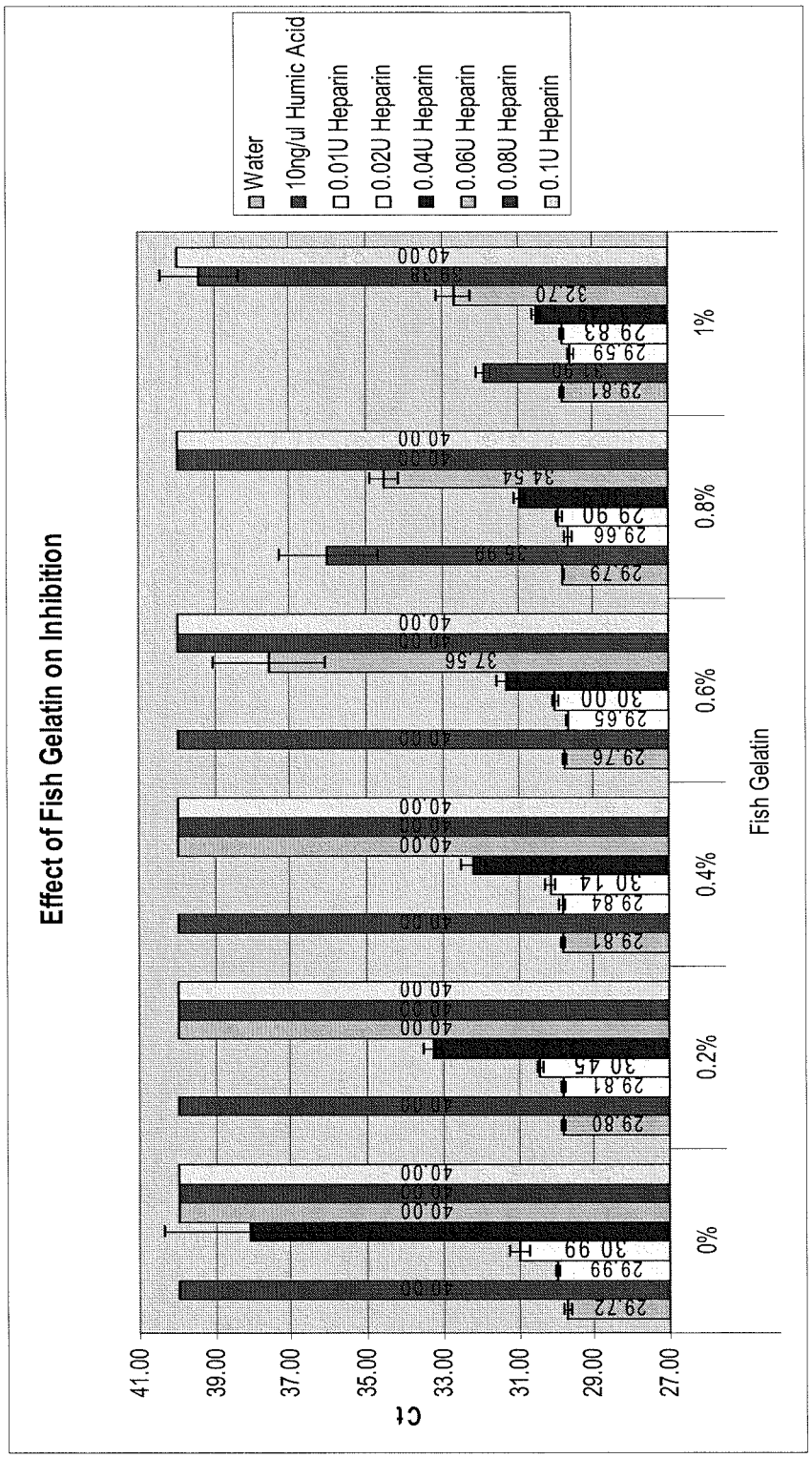
FIG. 1 depicts that fish gelatin is effective in increasing inhibitor tolerance to heparin and humic acid inhibition. The higher the concentration of fish gelatin used, the more tolerant (i.e., the lower the $C_t$) the reaction is to heparin and humic acid inhibition.

The present invention is directed to compositions, methods and kits for use in the production or analysis of nucleic acids. In particular, the present teachings offer several advantages compared to known compositions or methods for the generation or amplification of nucleic acids by, for example, RT-PCR. These advantages include, but are not limited to:

a) providing a true "one tube/one step" procedure for RT-PCR (versus having two separate reactions for the synthesis of DNA from an RNA template and the subsequent amplification of the DNA), which eliminates premixing or additional aliquotting steps since reverse transcriptase and DNA polymerase are contained in the master mix together and users do not have to add the reverse transcriptase to the master mix prior to performing RT-PCR;

b) providing compositions for use in nucleic acid synthesis (e.g. RT-PCR) that are in liquid or gel (i.e., not a solid) form at −20° C., which eliminates problems associated with multiple freeze-thaw cycles from repeated use;

c) providing more concentrated compositions for use in nucleic acid synthesis (e.g. RT-PCR), which allow for higher volume sample input if or when sample template concentrations are low (which is often the case for viral targets or forensic analysis);

d) providing compositions for use in nucleic acid synthesis (e.g. RT-PCR) that have increased tolerance to various PCR inhibitors;

e) providing compositions for use in nucleic acid synthesis (e.g. RT-PCR) that provide for maximal specificity and sensitivity;

f) providing nucleic acid synthesis (e.g. RT-PCR) compositions and methods that can be used with fast thermal cycling protocols for quicker read-outs;

e) providing nucleic acid synthesis (e.g. RT-PCR) compositions and methods which allow for the capability to multiplex (e.g., amplify a multiplicity of targets using a single sample (e.g., two targets on one sample) or multiple samples (e.g., two targets on two different samples) in a single reaction at substantially the same time); and f) providing multiplexed nucleic acid synthesis (e.g., RT-PCR) compositions and methods which allow for the type identification and quantification of nucleic acids (e.g., oncoviral nucleic acid) in a single reaction thereby reducing the amount of sample used as well as reducing costs and the amount of time it takes to obtain results.

Compositions

The present teachings provide compositions comprising a variety of components in various combinations. Such components can include one or more enzymes having reverse transcriptase activity, one or more DNA polymerases, or one or more PCR inhibitor blocking agents, such as bovine serum albumin (BSA) or fish gelatin. Additional components can also include, for example, one or more primers, one or more deoxyribonucleoside triphosphates, RNase inhibitor proteins (RIP), surfactants or detergents (such as, for example, TWEEN 20, NP-40 or CHAPS), or uracil DNA glycosylase (UDG), as well as suitable PCR buffer components, including, but not limited to, DMSO, glycerol and $Mg^{2+}$.

Such compositions can be formulated as concentrated stock solutions (e.g., 2×, 3×, 4×, 6×, 10×, etc.) or as working solutions (e.g., 1×). In some embodiments, having the composition as a concentrated (e.g., 4×) stock solution allows a greater amount of nucleic acid sample to be added (such as, for example, when the compositions are used for nucleic acid synthesis). These compositions can be used in the present methods to produce, analyze, quantitate and otherwise manipulate nucleic acid molecules using a one-step (or coupled) RT-PCR procedure.

In some embodiments, the compositions of the present teachings can be formulated as master mixes. Master mixes improve the efficiency and reduce the errors associated with the assembly of large number of reactions required for high-throughput analysis. In some embodiments, master mixes can contain combination of reagents common to all reactions. For example, the master mix can contain a buffer, a salt, such as $MgCl_2$, deoxynucleoside triphosphates (dNTPs), a labeled probe or dye, a reverse transcriptase, a thermostable DNA polymerase, and a PCR inhibitor blocking agent. Each reaction would then contain an aliquot of the common master mix and a specific target nucleic acid and primer pair. Master mixes can be manufactured and distributed as a concentrated solution. The master mix can then be diluted when final reactions are assembled.

In some embodiments, the present compositions can be packaged in a suitable container or vessel capable of holding the composition and which will not significantly interact with components of the composition. The container or vessel can be designed to permit easy dispensing of the dosage form by individuals or by a liquid handling instrument. The containers or vessels of such composition can be further packaged into multi-pack units.

Reverse Transcriptases

The compositions of the present teachings comprise polypeptides having reverse transcriptase activity (i.e., reverse transcriptases). In some preferred embodiments, the polypeptides having reverse transcriptase activity are thermostable. As used herein, the term "thermostable" refers to an enzyme that is heat stable or heat resistant. For the purposes of this disclosure, a thermostable polypeptide having reverse transcriptase activity can also be defined as a polypeptide having reverse transcriptase activity which retains a greater percentage of its activity after a heat treatment than is retained by a polypeptide having reverse transcriptase activity that has wild-type thermostability after an identical treatment.

According to some embodiments, enzymes having reverse transcriptase activity can be, for example, retroviral reverse transcriptases such as M-MLV reverse transcriptase, Rous Sarcoma Virus (RSV) reverse transcriptase, Human Immunodeficiency Virus (HIV) reverse transcriptase, Avian Myeloblastosis Virus (AMV) reverse transcriptase, Rous Associated Virus (RAV) reverse transcriptase, Myeloblastosis Associated Virus (MAV) reverse transcriptase, Avian Sarcoma Leukosis Virus (ASLV) reverse transcriptases, as well as Lentivirus reverse transcriptases, or corresponding mutants, variants or derivatives thereof having reverse transcriptase activity. As used herein, "mutants, variants, or derivatives" refer to all permutations of a chemical species, which can exist or be produced, that still retains the definitive chemical activity of that chemical species. Some preferred embodiments include enzymes that are RNase H+ enzymes such as, for example, RNase H+M-MLV or RNase H+AMV reverse transcriptases. Alternatively, the reverse transcriptases used in the present compositions can have reduced, substantially reduced, or eliminated RNase H activity (see, e.g., U.S. Pat. No. 7,078, 208, the disclosure of which is fully incorporated by reference in its entirety). RNase H is a processive 5' and 3' ribonuclease that is specific for the RNA strand of RNA-DNA hybrids (Perbal, *A Practical Guide to Molecular Cloning*, New York: Wiley & Sons, pp.23-24 (1984)). RNase H activity can be determined by a variety of assays, such as those described, for example, in U.S. Pat. No. 5,244,797, in Kotewicz, et al., *Nucl. Acids Res.* 16:265-277 (1988) and in Gerard, et al., FOCUS (Life Technologies) 14:91-93 (1992), the disclosures of which are fully incorporated herein by reference in there entireties.

Additional enzymes having reverse transcriptase activity can be used in accordance with the present teachings, such as *Thermus thermophilus* (Tth) reverse transcriptase, which has reverse transcriptase activity in the presence of $Mn^{2+}$ and DNA polymerase activity in the presence of $Mg^{2+}$ (Myers and Gelfand, Biochemistry 30:7661-7666 (1991), the disclosure of which is fully incorporated herein by reference in its entirety). Methods for the isolation or purification of reverse transcriptases have been described, for example, in U.S. Pat. Nos. 4,943,531 and 5,017,492, the disclosures of which are fully incorporated herein by reference in their entireties. Such enzymes can also be available commercially (for example, SUPERSCRIPT II™, SUPERSCRIPT III™ and ArrayScript available from Life Technologies, Carlsbad, Calif.). It is to be understood that a variety of reverse transcriptases can be used in the present teachings, including reverse transcriptases not specifically disclosed above, without departing from the scope or preferred embodiments thereof.

In accordance with the present teachings, any number of mutations can be made to the reverse transcriptases and, in a preferred embodiment, multiple mutations can be made which result in an increased reverse transcriptase stability or functionality. Enzymes for use herein can also include those in which terminal deoxynucleotidyl transferase (TdT) activity has been reduced, substantially reduced, or eliminated. Reverse transcriptases which exhibit such increased or decreased functionalities are described in, for example, U.S. Pat. Nos. 7,056,716 and 7,078,208 (the disclosures of which are fully incorporated by reference in their entireties). In some embodiments, such mutated reverse transcriptases can include reverse transcriptases with one or more alterations at amino acid positions equivalent or corresponding to Y64, R116, D124, H126, Y133, K152, Q190, T197, H204, V223, M289, T306, or F309 of M-MLV reverse transcriptase. Such mutations can include point mutations, frame shift mutations, deletions and insertions, with one or more (e.g., one, two, three, four, five, ten, twelve, fifteen, twenty, thirty, etc.) point mutations preferred.

Mutations can be introduced into the reverse transcriptases of the present teachings using any methodology known to those of skill in the art. In one embodiment, mutant or modified reverse transcriptases can be made by recombinant techniques. A number of cloned reverse transcriptase genes are available or can be obtained using standard recombinant techniques (see, e.g., U.S. Pat. No. 5,668,005 and PCT Publication No. WO 98/47912). For example, oligonucleotide site-directed mutagenesis can be used to create a mutant polymerase which allows for all possible classes of base pair changes at any determined site along the encoding DNA molecule. Alternatively, mutations can also be introduced randomly by, for example, conducting a PCR reaction in the presence of manganese as a divalent metal ion cofactor.

Polypetides having reverse transcriptase activity can be added to the present compositions to give a final concentration in a working solution of about 0.001 U/µL to about 500 U/µL, about 0.005 U/µL to about 100 U/µL, about 0.01 U/µL to about 50 U/µL, about 0.05 U/µL to about 20 U/µL, about 0.1 U/µL to about 10 U/µL, about 0.2 U/µL to about 5 U/µL, or preferably at a concentration of about 0.2 U/µL, about 0.4 U/µL, about 0.8 U/µL, about 1.0 U/µL, about 1.2 U/µL, about 1.4 U/µL, about 1.8 U/µL, about 2 U/µL, about 3 U/µL, about 4 U/µL, or about 5 U/µL.

Polymerases

The compositions of the present teachings can also comprise one or more polymerases. Such polymerases can be any enzyme capable of replicating a DNA molecule. Preferably, the DNA polymerases are thermostable DNA polymerases. Thermostable DNA polymerases, as used herein, are not irreversibly inactivated when subjected to elevated temperatures for the time necessary to effect destabilization of single-stranded nucleic acids or denaturation of double-stranded nucleic acids during PCR amplification. Irreversible denaturation of the enzyme refers to substantial loss of enzyme activity. Preferably a thermostable DNA polymerase will not irreversibly denature at about 90°-100° C. under conditions such as is typically required for PCR amplification.

DNA polymerases in accordance with the present teachings can be isolated from natural or recombinant sources, by techniques that are well-known in the art (see, e.g., PCT Publication Nos. WO 92/06200; WO 96/10640; U.S. Pat. Nos. 5,455,170; 5,912,155; and 5,466,591, the disclosures of which are fully incorporated herein by reference in their entireties), from a variety of thermophilic bacteria that are available commercially (for example, from American Type Culture Collection, Rockville, Md.) or can be obtained by recombinant DNA techniques (see, e.g., PCT Publication No. WO 96/10640 and U.S. Pat. No. 5,912,155). Suitable for use as sources of thermostable polymerases or the genes thereof for expression in recombinant systems are, for example, the thermophilic bacteria *Thermus thermophilus, Thermococcus litoralis, Pyrococcus furiosus, Pyrococcus woosii* and other species of the *Pyrococcus* genus, *Bacillus sterothermophilus, Sulfolobus acidocaldarius, Thermoplasma acidophilum, Thermus flavus, Thermus ruber, Thermus brockianus, Thermotoga neapolitana, Thermotoga maritima* and other species of the *Thermotoga* genus, and *Methanobacterium thermoautotrophicum*, and mutants, variants or derivatives thereof. It is to be understood, however, that DNA polymerases from other organisms can also be used herein without departing from the scope or preferred embodiments thereof. As an alternative to isolation, DNA polymerases are available commercially from, for example, Life Technologies (Carlsbad, Calif.), New England BioLabs (Beverly, Mass.), Finnzymes Oy (Espoo, Finland), Stratagene (La Jolla, Calif.), Boehringer Mannheim Biochemicals (Indianapolis, Ind.) and Perkin Elmer Cetus (Norwalk Conn.).

Particularly preferred thermostable DNA polymerases for use in the present compositions and methods include, but are not limited to, Taq, Tne, Tma, Tfi/VENT, DEEPVENT, Pfu, Pwo, Tfi or Tth DNA polymerases, or mutants, variants or derivatives thereof having DNA polymerase activity. Taq DNA polymerase and mutant forms thereof are commercially available, for example, from Life Technologies (Carlsbad, Calif.), or can be isolated from their natural source, the thermophilic bacterium *Therms aquaticus*, as described previously (see, e.g., U.S. Pat. Nos. 4,889,818 and 4,965,188, the disclosures of which are incorporated herein by reference in their entireties). Tne DNA polymerase can be isolated from its natural source, the thermophilic bacterium *Thermotoga neapolitana* (see, e.g., PCT Publication No. WO 96/10640 and U.S. Pat. No. 5,912,155), and Tma DNA polymerase can be isolated from its natural source, the thermophilic bacterium *Thermotoga maritima* (see, e.g., U.S. Pat. No. 5,374,553, the disclosure of which is incorporated herein by reference in its entirety). It is to be understood that a variety of DNA polymerases can be used in the present compositions, methods and kits, including polymerases not specifically disclosed herein, without departing from the scope or preferred embodiments thereof.

Methods for producing mutants and derivatives of thermophilic DNA polymerases, particularly of Tne and Tma polymerases are disclosed, for example, in U.S. application Ser. Nos. 08/689,807 and 08/689,818, both filed Sept. 6, 1996, both of which are incorporated by reference herein in their entireties. Tfi, Tli/VENT, and DEEPVENT are available commercially (e.g., from New England BioLabs; Beverly, Mass.), or can be produced as described (Bej and Mahbubani, in: *PCR Technology: Current Innovations*, Griffin, H. G., and Griffin, A. M., eds., CRC Press, pp. 219-237 (1994) for Tli/VENT; Flaman, et al., *Nucl. Acids Res.* 22:3259-3260 (1994) for DEEPVENT). Thermostable DNA polymerases of the present invention can be added to the present compositions to give a final concentration in a working solution of about 0.0001 U/μL to about 50 U/μL, about 0.0005 U/μL to about 10 U/μL, about 0.001 U/μL to about 5 U/μL, about 0.005 U/μL to about 2 U/μL, about 0.01 U/μL to about 1 U/μL, about 0.02 U/μL to about 0.5 U/μL, or preferably at a concentration of about 0.02 U/μL, about 0.04 U/μL, about 0.08 U/μL, about 0.1 U/μL, about 0.12 U/μL, about 0.14 U/μL, about 0.18 U/μL, about 0.2 U/μL, about 0.3 U/μL, about 0.4 U/μL, or about 0.5 U/μL.

In some embodiments, the concentration of DNA polymerases can be determined as a ratio of the concentration of the enzymes having reverse transcriptase activity to the concentration of the enzymes having DNA polymerase activity. Thus, in some compositions the unit ratio of the reverse transcriptase enzymes to the DNA polymerase enzymes can range from about 500 U/μL to about 0.001 U/μL, about 250 U/μL to about 0.005 U/μL, about 100 U/μL to about 0.01 U/μL, about 50 U/μL to about 0.05 U/μL, about 25 U/μL to about 0.1 U/μL, or preferably about 5 U/μL to about 0.5 U/μL. Of course, other suitable ratios of unit activities of reverse transcriptase enzymes to DNA polymerases suitable for use in the present compositions, methods and kits will be apparent to one of ordinary skill in the art.

PCR Inhibitor Blocking Agents

In accordance with the present teachings, one or more PCR inhibitor blocking agents can be added to the present compositions to assist in overcoming the inhibition of PCR reactions by a variety of compounds often found in samples used for nucleic acid preparation, isolation or purification. Such inhibitors include, for example, heparin (blood); hematin (blood); EDTA (blood); citrate (blood); immunoglobin G (blood, serum); humic acid (soil, feces); lactoferrin (milk, saliva, other secretory fluids); urea (urine); plant polysaccharides (plants); melanin (skin, hair); myoglobin (tissue); and indigo dye (textiles). The addition of PCR inhibitor blocking agents, both individually and in combination, can increase tolerance to such PCR inhibitor contaminants. Thus, the present compositions can further comprise agents that work alone or in combination to increase tolerance to various PCR inhibitors including, for example, humic acid, hematin, and heparin.

Such PCR inhibitor blocking agents for use in the present teachings can include proteins such as, but not limited to, albumin (e.g. bovine serum albumin (BSA), recombinant BSA and albumins derived from other species), gelatin (e.g., human recombinant gelatin, fish gelatin and gelatins derived from other species), and DNA-binding proteins (e.g., phage T4 gene 32 (T4gP32)), or peptide or polypeptide variants, fragments or derivatives thereof. Other non-protein based PCR inhibitor blocking agents for use in the present teachings include, for example, deferoxamine mesylate. Some preferred proteins for use as PCR inhibitor blocking agents include bovine serum albumin (BSA), fish gelatin, and T4gP32 proteins. Particularly preferred for use in the present compositions and methods are combinations of the PCR inhibitor blocking agents, BSA and fish gelatin.

In some embodiments, fish gelatin is effective at reducing PCR inhibition by at least humic acid and heparin, and BSA is effective at reducing PCR inhibition by at least humic acid and hematin. In some embodiments this phenomenon is demonstrated by lower $C_t$ values. As used herein the term "$C_t$" or "$C_t$ value" refers to threshold cycle and signifies the cycle of a PCR amplification assay in which signal from a reporter that is indicative of amplicon generation (e.g., fluorescence) first becomes detectable above a background level. In some embodiments, the threshold cycle or "$C_t$" is the cycle number at which PCR amplification becomes exponential.

According to various embodiments, a $C_t$ value can be determined using a derivative of a PCR curve. For example, a first, second, or nth order derivative method can be performed on a PCR curve in order to determine a $C_t$ value. In various embodiments, a characteristic of a derivative can be used in the determination of a $C_t$ value. Such characteristics can include, but are not limited to, a positive inflection of a second derivative, a negative inflection of a second derivative, a zero crossing of the second derivative, or a positive inflection of a first derivative. In various embodiments, a $C_t$ value can be determined using a thresholding and baselining method. For example, an upper boundary to an exponential phase of a PCR curve can be established using a derivative method, while a baseline for a PCR curve can be determined to establish a lower boundary to an exponential phase of a PCR curve. From the upper and lower boundaries of a PCR curve, a threshold value can be established from which a $C_t$ value is determined. Other methods for the determination of a $C_t$ value include, but are not limited to, various embodiments of a fit point method, and various embodiments of a sigmoidal method (See, e.g., U.S. Pat. Nos. 6,303,305; 6,503,720; 6,783,934; 7,228,237 and U.S. Application Publication No. 2004/0096819; the disclosures of which are herein incorporated by reference in their entireties).

In some embodiments, the higher the concentration of BSA used, the more tolerant the reaction is to hematin and humic acid inhibition. However, in some embodiments with increasing amounts of BSA, dRn decreases and baseline value (or background signal) increases. As used herein, the term "dRn" or "delta Rn" refers to the difference in the normalized reporter signal (Rn) subtracted from the background signal (baseline) which is then normalized by a passive reference signal. Delta Rn can be determined by the formula [$Rn^+ - Rn^-$], where $Rn^+$ is the Rn value for a reaction involving all components, including the template, and $Rn^-$ is the value for an unreacted sample.

Surprisingly, by using such PCR inhibitor blocking agents in combination, such as fish gelatin and BSA, the level of inhibitor tolerance is enhanced without a significant reduction in PCR performance. This property allows for the use of a lesser amount of each agent, when combined, to achieve the same level of inhibitor tolerance as compared to using any of the PCR inhibitor blocking agents individually, thus maximizing tolerance (as demonstrated by lower CO, and minimizing the reduction of dRn and increased baseline values. Thus, the addition of PCR inhibitor blocking agents, including but not limited to, fish gelatin, BSA, or combinations thereof, are effective in alleviating or eliminating inhibition of a variety of PCR inhibitors typically found in samples used for nucleic acid analysis.

PCR inhibitor blocking compounds or agents can be added to the present compositions to give a final concentration in a working solution of about 1 ng/µL to about 10,000 ng/µL, about 50 ng/µL to about 8000 ng/µL, about 100 ng/µL to about 6000 ng/µL, about 200 ng/µL to about 3000 ng/µL or preferably about 500 ng/µL to about 1000 ng/µL. PCR inhibitor blocking agents can also be added as a percentage of the final concentration in a working solution, for example, from about 0.001% to about 15%, about 0.05% to about 10%, about 0.01% to about 5%, or preferably about 0.1% to about 1%.

In some aspects, PCR inhibitor blocking agents can reduce the amount of PCR inhibition by such PCR inhibitors by at least 1 to 100% compared to the level of inhibition observed in the absence of such PCR inhibitor blocking agents. For example, inhibition can be reduced by at least about 1%, about 2%, about 5%, about 10%, about 20%, about 50%, about 75%, about 100% or any percentage in between.

Nucleotides

The compositions of the present teachings can further comprise one or more nucleotides (e.g., deoxynucleoside triphosphates (dNTPs)). The nucleotide components of the present compositions serve as the "building blocks" for newly synthesized nucleic acids, being incorporated therein by the action of the reverse transcriptases or DNA polymerases. Examples of nucleotides suitable for use in the present compositions include, but are not limited to, dUTP, dATP, dTTP, dCTP, dGTP, dITP, 7-deaza-dGTP, a-thio-dATP, a-thio-dTTP, a-thio-dGTP, a-thio-dCTP or derivatives thereof, all of which are available commercially from sources including Life Technologies (Carlsbad, Calif.), New England BioLabs (Beverly, Mass.) and Sigma Chemical Company (Saint Louis, Mo.). Such dNTPs may be unlabeled, or they may be detectably labeled by coupling them by methods known in the art with radioisotopes (e.g., $^{3}$H, $^{14}$C, $^{32}$P or $^{35}$S),), vitamins (e.g., biotin), fluorescent moieties (e.g., fluorescein, rhodamine, Texas Red, or phycoerythrin), chemiluminescent labels, dioxigenin (DIG) and the like. Labeled dNTPs may also be obtained commercially, for example from Life Technologies (Carlsbad, Calif.) or Sigma Chemical Company (Saint Louis, Mo.).

Specific examples of fluorescently labeled nucleotides include [R6G]dUTP, [TAMRA]dUTP, [R110]dCTP, [R6G] dCTP, [TAMRA]dCTP, [JOE]ddATP, [R6G]ddATP, [FAM] ddCTP, [R110]ddCTP, [TA MRA]ddGTP, [ROX]ddTTP, [dR6G]ddATP, [dR110]ddCTP, [dTAMRA]ddGTP, and [dROX]ddTTP available from Life Technologies, Foster City, Calif. FluoroLink™ DeoxyNucleotides, FluoroLink Cy3-dCTP, FluOroLink Cy5-dCTP, FluoroLink Fluor X-dCTP, FluoroLink Cy3-dUTP, and FluoroLink Cy5-dUTP available from Amersham Arlington Heights, Ill.; Fluorescein-15-dATP, Fluorescein-12-dUTP, Tetramethyl-rodamine-6-dUTP, IR.sub.770-9-dATP, Fluorescein-12-ddUTP, Fluorescein-12-UTP, and Fluorescein-15-2'-dATP available from Boehringer Mannheim Indianapolis, Ind.; and Chroma-Tide™ Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. DIG labels include digoxigenin-11-UTP available from Boehringer Mannheim, Indianapolis, Ind., and biotin labels include biotin-21-UTP and amino-7-dUTP available from Clontech, Palo Alto, Calif. The term nucleotide includes modified nucleotides. Many examples of modified nucleotides are disclosed in U.S. Pat. No. 6,200,757 (the disclosure of which is herein incorporated by reference in its entirety).

In some embodiments of the present compositions, dNTPs can be added to give a final concentration in a working solution of each dNTP of about 0.001 mM to about 100 mM, about 0.01 mM to about 10 mM, about 0.1 mM to about 1 mM, or preferably about 0.2 mM to about 0.6 mM.

Primers

In addition to nucleotides, the present compositions can comprise one or more primers which facilitate the synthesis of a first DNA molecule complementary to all or a portion of an RNA template (e.g., a single-stranded cDNA molecule). Such primers can also be used to synthesize a DNA molecule complementary to all or a portion of the first DNA molecule, thereby forming a double-stranded cDNA molecule. Additionally, these primers can be used in amplifying nucleic acid molecules in accordance with the present teachings. Oligonucleotide primers can be any oligonucleotide of two or more (e.g., 2, 3, 4, 5, 10, 20, etc.) nucleotides in length. Such primers include, but are not limited to, target-specific primers (which are preferably gene-specific primers), oligo (dT) primers, random primers or arbitrary primers. Additional primers that can be used for amplification of the DNA molecules according to the methods disclosed herein will be apparent to one of ordinary skill in the art. It is to be understood that a vast array of primers can be useful in the present compositions, methods and kits, including those not specifically disclosed herein, without departing from the scope or preferred embodiments thereof.

In some embodiments of the disclosed compositions, the final concentration of primers in a working solution can range from about 25 nM to about 2000 nM, such as about 50 nM to about 1700 nM, about 75 nM to about 1500 nM, about 100 nM to about 1200 nM, about 200 nM to about 1000 nM, or any range in between. In some exemplary embodiments, the concentration of the primers is between about 400 nM to about 900 nM.

Probes

In accordance with the present teachings, the compositions can further comprise probes for the detection of target nucleic acids. Various probes are known in the art, for example, TaqMan® probes (see, e.g., U.S. Pat. No. 5,538,848), various stem-loop molecular beacons (see, e.g., U.S. Pat. Nos. 6,103, 476 and 5,925,517 and Tyagi and Kramer, *Nature Biotechnology* 14:303-308 (1996)), stemless or linear beacons (see, e.g., PCT Publication No. WO 99/21881), PNA Molecular Beacons™ (see, e.g., U.S. Pat. Nos. 6,355,421 and 6,593, 091), linear PNA beacons (see, e.g., Kubista et al., *Proceedings in SPIE* 4264:53-58 (2001)), non-FRET probes (see, e.g., U.S. Pat. No. 6,150,097), Sunrise®/Amplifluor® probes (U.S. Pat. No. 6,548,250), stem-loop and duplex Scorpion™ probes (see, e.g., Solinas et al., *Nucleic Acids Research* 29:E96 (2001) and U.S. Pat. No. 6,589,743), bulge loop probes (see, e.g., U.S. Pat. No. 6,590,091), pseudo knot probes (see, e.g., U.S. Pat. No. 6,589,250), cyclicons (see, e.g., U.S. Pat. No. 6,383,752), MGB Eclipse™ probes (Epoch Biosciences, Bothell, Wash.), hairpin probes (see, e.g., U.S. Pat. No. 6,596,490), peptide nucleic acid (PNA) light-up probes, self-assembled nanoparticle probes and ferrocene-modified probes described, for example, in U.S. Pat. No. 6,485,901; Mhlanga et al., *Methods* 25:463-471 (2001); Whitcombe et al., *Nature Biotechnology* 17:804-807 (1999); Isacsson et al., *Molecular Cell Probes* 14:321-328 (2000); Svanvik et al., *Anal. Biochem.* 281:26-35 (2000); Wolffs et al., *Biotechniques* 766:769-771 (2001); Tsourkas et al., *Nucleic Acids Research* 30:4208-4215 (2002); Riccelli et al., *Nucleic Acids Research* 30:4088-4093 (2002); Zhang et al., *Shanghai* 34:329-332 (2002); Maxwell et al., *J. Am. Chem. Soc.* 124:9606-9612 (2002); Broude et al., *Trends Biotechnol.* 20:249-56 (2002); Huang et al., *Chem Res. Toxicol.* 15:118-126 (2002); and Yu et al., *J. Am. Chem. Soc.* 14:11155-11161 (2001). Probes can comprise reporter dyes such as, for example, 6-carboxyfluorescein (6-FAM) or tetrachlorofluorescin (TET) and the like. Detector probes can also comprise quencher moieties such as tetramethylrhodamine (TAMRA), Black Hole Quenchers (Biosearch Technologies, Novato, Calif.), Iowa Black (IDT, Coralville, Iowa), QSY quencher (Molecular Probes, Eugene, Oreg.), and DABSYL and DABCEL sulfonate/carboxylate Quenchers (Epoch Biosciences, Bothell, Wash.) and the like. Probes can also comprise two probes, wherein for example a fluorophore is on one probe, and a quencher on the other, wherein hybridization of the two probes together on a target quenches the signal, or wherein hybridization on a target alters the signal signature via a change in fluorescence.

Exemplary detectable labels include, for instance, a fluorescent dye or fluorphore (e.g., a chemical group that can be excited by light to emit fluorescence or phosphorescence), "acceptor dyes" capable of quenching a fluorescent signal from a fluorescent donor dye, and the like. Suitable detectable labels may include, for example, fluoresceins (e.g., 5-carboxy-2,7-dichlorofluorescein; 5-Carboxyfluorescein (5-FAM); 5-HAT (Hydroxy Tryptamine); 6-HAT; 6-JOE; 6-carboxyfluorescein (6-FAM); FITC); Alexa fluors (e.g., 350, 405, 430, 488, 500, 514, 532, 546, 555, 568, 594, 610, 633, 635, 647, 660, 680, 700, 750); BODIPY® fluorophores (e.g., 492/515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE), coumarins (e.g., 7-amino-4-methylcoumarin, AMC, AMCA, AMCA-S, AMCA-X, ABQ, CPM methylcoumarin, coumarin phalloidin, hydroxycoumarin, CMFDA, methoxycoumarin), calcein, calcein AM, calcein blue, calcium dyes (e.g., calcium crimson, calcium green, calcium orange, calcofluor white), Cascade Blue, Cascade Yellow; Cy™ dyes (e.g., 3, 3.18, 3.5, 5, 5.18, 5.5, 7), cyan GFP, cyclic AMP Fluorosensor (FiCRhR), fluorescent proteins (e.g., green fluorescent protein (e.g., GFP, EGFP), blue fluorescent protein (e.g., BFP, EBFP, EBFP2, Azurite, mKalamal), cyan fluorescent protein (e.g., ECFP, Cerulean, CyPet), yellow fluorescent protein (e.g., YFP, Citrine, Venus, YPet), FRET donor/acceptor pairs (e.g., fluorescein/tetramethylrhodamine, IAEDANS/fluorescein, EDANS/dabcyl, fluorescein/fluorescein, BODIPY® FL/BODIPY® FL, Fluorescein/QSY7 and QSY9), LysoTracker and LysoSensor (e.g., LysoTracker Blue DND-22, LysoTracker Blue-White DPX, LysoTracker Yellow HCK-123, LysoTracker Green DND-26, LysoTracker Red DND-99, LysoSensor Blue DND-167, LysoSensor Green DND-189, LysoSensor Green DND-153, LysoSensor Yellow/Blue DND-160, LysoSensor Yellow/Blue 10,000 MW dextran), Oregon Green (e.g., 488, 488-X, 500, 514); rhodamines (e.g., 110, 123, B, B 200, BB, BG, B extra, 5-carboxytetramethylrhodamine (5-TAMRA), 5 GLD, 6-Carboxyrhodamine 6G, Lissamine, Lissamine Rhodamine B, Phallicidine, Phalloidine, Red, Rhod-2, 5-ROX (carboxy-X-rhodamine), Sulphorhodamine B can C, Sulphorhodamine G Extra, Tetramethylrhodamine (TRITC), WT), Texas Red, Texas Red-X, VIC and other labels described in, e.g., US Publication No. 2009/0197254), among others as would be known to those of skill in the art.

In some embodiments, the probes are designed according to the methods and principles described in, for example, U.S. Pat. No. 6,727,356 (the disclosure of which is incorporated herein by reference in its entirety). Some probes can be sequence-based, for example 5' nuclease probes and some, such as SYBR® Green can be non-sequence specific DNA-binding dyes. In some preferred embodiments, the detector probe is a TaqMan® probe (Applied Biosystems, Foster City, Calif.). It is to be understood that a wide variety of probes are known in the art that can be used in the present compositions, methods and kits, including those not specifically disclosed herein.

In some embodiments of the disclosed compositions, the final probe concentration in a working solution can range from about 5 nM to about 750 nM, such as about 10 nM to about 600 nM, about 25 nM to about 500 nM, about 50 nM to about 400 nM, about 75 nM to about 300 nM, or any number in between. In some exemplary embodiments, the probe concentration is between about 100 nM to about 250 nM.

Additional Components/Additives

Other additives capable of facilitating or enhancing reverse transcription, amplification, or a combination of both reactions (e.g., agents for facilitating or enhancing RT-PCR), other than those disclosed herein, are known in the art. In accordance with the present compositions and methods, one or more of these additives can be incorporated in the present compositions to optimize the generation and replication of nucleic acids from a ribonucleic acid or deoxyribonucleic acid templates. Additives can be organic or inorganic compounds. Some additives useful in the present compositions, methods and kits include polypeptides as well as nonpolypeptide additives. Such additives can include, for example, RNase inhibitor protein (RIP), uracil DNA glycosylase (UDG), lectins, *E. coli* single-stranded binding (SSB) protein, tRNA, rRNA, 7-deaza-2'-deoxyguanosine (dC7GTP), sulfur-containing compounds, acetate-containing compounds, dimethylsulfoxide (DMSO), glycerol, formamide, betaine, tetramethylammonium chloride (TMAC), polyethylene glycol (PEG), various surfactants or generally any Zwitterionic, cationic, anionic or non-ionic (e.g., TWEEN 20, NP-40, Tritin X-100, and CHAPS) detergents, ectoine, sodium azide, kathon, and polyols, to name just a few. Those of ordinary skill in the art will be able to identify additional additives for use in accordance with the present compositions, methods and kits.

The compositions and methods in accordance with the present teachings can also include additional "hot start" PCR components or steps, as a means to further prevent, reduce or eliminate nonspecific nucleic acid synthesis. The term "hot start," as used herein, refers to any modified form of PCR which prevents non-specific amplification of DNA by inactivating the polymerase activity at lower annealing temperatures and reactivating or activating the polymerase activity at higher temperatures during the extension phase. Many hot start mechanisms are well known to those of ordinary skill in the art and will be readily selectable based on their ability to work in accordance with the present teachings. In some embodiments, the hot start components that can be optionally added to the present compositions can include, for example, an antibody or antibodies, specially designed primers, competitive oligonucleotides or aptamers, polymerase binding proteins or sequestration beads. Sequestration wax beads for hot start PCR are commercially available, e.g., AmpliWax® PCR Gem 100 and AmpliWax® PCR Gem 50 (Applied Biosystems, Foster City, Calif.). Selection of a suitable aptamer can be performed by a method known in the art or a commercially available aptamer can be used. Similarly, selection of a suitable primer can be performed by a method known in the art or a commercially available primer can be used. In some cases a suitable primer can be a primer specially designed to have secondary structures that prevent the primers from annealing until cycling temperatures denature them. Antibodies for hot start PCR can be generated or selected by a method known in the art. Alternatively, a commercially available antibody can be used, for example, the TaqStart® Antibody (Clontech, Mountain View, Calif.) which is effective with any Taq-derived DNA polymerase, including native, recombinant, and N-terminal deletion mutants. An appropriate concentration of the reagent for hot start PCR in the assembled PCR can be determined by a method known in the art or, for a commercial product, as suggested by the manufacturer. Other examples of hot start components or mechanisms used for this purpose are known in the art (see, e.g., U.S. Pat. No. 6,403,341 and U.S. Patent Application Publication No. 2009/0269766, the disclosures of which are fully incorporated herein by reference in their entireties.)

The compositions and methods in accordance with the present teachings can also include a passive reference control. In some embodiments the passive reference control is used to minimize sample-to-sample or well-to-well variations in quantitative real-time nucleic acid-detection assays and can be included at a concentration allowing its use as detectable control. In an embodiment, a reference chromophore, specifically a fluorophore, is included as the passive reference control. In an embodiment, the reference chromophore is the dye ROX (Invitrogen, Carlsbad, Calif.). In one embodiment, ROX can be included in the composition at a concentration in a working solution of about 40 nM to about 80 nM, specifically about 60 nM.

It is to be understood that a wide variety of additional components known in the art can be useful in the present compositions, methods and kits, including those not specifically disclosed herein. Those of skill in the art will also understand the methods required to determine the particular conditions or concentrations to use of each component in accordance with the present teachings.

Buffers and Salts

To form the compositions of the present teachings, one or more reverse transcriptases and one or more DNA polymerases are preferably mixed in a buffered salt solution. In accordance with the teachings, buffer agents or salt solutions used in the present compositions and reaction mixtures provide appropriate pH and ionic conditions to maintain stability of the enzymes having reverse transcriptase activity or DNA polymerase activity. The terms "stable" and "stability," as used herein, generally mean the retention by a composition, such as an enzyme composition, of at least 70%, preferably at least 80%, and most preferably at least 90%, of the original enzymatic activity (in units) after the enzyme or composition containing the enzyme has been stored for about 3 days at a temperature of about room temperature (e.g., about 20° C. to about 25° C.), about one week at a temperature of about 4° C., about two to six months at a temperature of about –20° C., and about six months or longer at a temperature of about –80° C. Examples of such buffering agents can include, for example, TRIS, TRICINE, BIS-TRICINE, HEPES, MOPS, TES, TAPS, PIPES, and CAPS. Examples of such salt solutions can include, for example, potassium chloride, potassium acetate, potassium sulfate, ammonium sulfate, ammonium chloride, ammonium acetate, magnesium chloride, magnesium acetate, magnesium sulfate manganese chloride, manganese acetate, manganese sulfate, sodium chloride, sodium acetate, lithium chloride and lithium acetate. It is to be understood that a wide variety of buffers and salt solutions are known in the art that can be used in the present compositions, methods and kits, including those not specifically disclosed herein.

In some embodiments, the compositions can be provided as a concentrated stock. As used herein, the term "concentrated stock" means at a concentration that requires further dilution in order to achieve optimal concentration for use in a solution to perform a particular function (such as reverse transcription of nucleic acids). As used herein, "working solution" can be used to refer to the solution having an optimal concentration to perform a particular function. For example, compositions of the present teachings can be stock solutions of about 2×, about 3×, about 4×, about 5×, about 6×, about 10×, and so on. In some preferred embodiments, the compositions can require greater than 2×, greater than 3×, greater than 4×, greater than 5×, greater than 6×, greater than 10×, and so on, dilution to be at working, or optimal, concentration for use in nucleic acid synthesis methods.

Nucleic Acid Samples

Nucleic acid samples suitable for use in accordance with the present teachings can include any quantity of one or more nucleic acid molecules. In some embodiments, such nucleic acid molecules can be extracellular nucleic acid molecules. In other embodiments, such nucleic acid molecules can be derived from cells. In general, such cells can include, for example, any prokaryotic, eukaryotic or plant cell. Such cells can be normal cells, diseased cells, transformed cells, established cells, progenitor cells, precursor cells, fetal cells, embryonic cells, bacterial cells, yeast cells, animal cells (including human cells), avian cells, plant cells and the like, or tissue isolated from a plant or an animal (e.g., human, cow, pig, mouse, sheep, horse, monkey, canine, feline, rat, rabbit, bird, fish, insect, etc.). In some preferable embodiments, nucleic acid molecules can also be isolated from viruses. In accordance with the present methods, such nucleic acid samples can be extracted from a variety of sources. These include, but are not limited to, for example clothing, soil, skin, hair, blood, serum, feces, milk, saliva, urine, or other secretory fluids. These sources can also contain compounds that inhibit PCR amplification.

In accordance with the present teachings, the nucleic acid samples or templates can be any ribonucleic acid (RNA) or deoxyribonucleic acid (DNA) of interest, known or unknown, to the practitioner. Nucleic acid samples can be artificially synthesized or isolated from natural sources. In some preferred embodiments the nucleic acid sample is single stranded. Alternatively the nucleic acid sample can be double stranded. In some embodiments the nucleic acid sample can be messenger RNA (mRNA), RNA, genomic DNA (gDNA) or cDNA. Many nucleic acid sample preparation or isolation methods are known in the art. A variety of nucleic acid isolation or preparation kits are also available commercially, for example, MagMAX™ (Applied Biosystems, Foster City, Calif.), iPrep™ (Invitrogen, Carlsbad, Calif.) and QIAmp MinElute (Qiagen, San Diego, Calif.).

Methods of Nucleic Acid Synthesis

In accordance with the present teachings, the above compositions can be used in methods for nucleic acid synthesis of one or more (e.g., one, two, three, four, five, ten, twelve, fifteen, twenty, etc.) nucleic acid molecules comprising mixing one or more (e.g., one, two, three, four, five, ten, twelve, fifteen, twenty, etc.) nucleic acid templates. In some embodiments, RNA or mRNA can serve as the template for nucleic acid synthesis by one or more reverse transcriptase. Alternatively, cDNA or gDNA can serve as the template for nucleic acid synthesis by one or more polymerases. In some embodiments, such methods can comprise incubating the mixture comprising one or more reverse transcriptases or one or more polymerases under conditions sufficient to make a nucleic acid molecule or molecules complementary to all or a portion of the one or more (e.g., one, two, three, four, five, ten, twelve, fifteen, twenty, thirty, etc.) templates. To make the nucleic acid molecule or molecules complementary to the one or more templates, a primer (e.g., an oligo(dT) primer) and one or more nucleotides are preferably used for nucleic acid synthesis in the 5' to 3' direction.

Additional embodiments provide methods for amplifying a nucleic acid molecule comprising contacting the nucleic acid molecule with a polymerase. In some embodiments, simplex (i.e., single) amplification reactions are performed at one time in a single reaction or vessel. In other embodiments, multiplex (e.g., 2, 3, 4, 5, 10, 100, 1000 and so on) amplification reactions are performed at one time in a single reaction or vessel. As used herein, "multiplex" or "multiplexing" refers to the essentially simultaneous amplification or analysis of multiple targets in a single reaction. In some embodiments, multiplexing can involve the amplification of a single or multiple targets from one or multiple sample input(s) and an exogenous control target from one exogenous control template within the same reaction vessel (e.g., tube, compartment, well). In some preferred embodiments, such methods can comprise one or more polymerase chain reactions (PCRs). For example, such multiplex PCR reactions can comprise the essentially simultaneous amplification of greater than 1, greater than 2, greater than 3, greater than 5, greater than 10, greater than 20, greater than 50, greater than 100, greater than 1000, etc. nucleic acid targets within the same reaction.

In some embodiments, such PCR methods can be quantitative PCR (qPCR) or end point PCR amplification methods. In some preferred embodiments, such PCR methods are real time PCR amplification methods. In some embodiments, such PCR methods can comprise thermal cycling, which can comprise alternating heating and cooling of the mixture sufficient to amplify the DNA molecule and which most preferably comprises alternating from a first temperature range of from about 90° C. to about 100° C., to a second temperature range of from about 45° C. to about 75° C., from about 50° C. to about 70° C., from about 55° C. to about 65° C., or preferably at about 58° C., at about 59° C., at about 60° C., at about 61° C. or at about 62° C. In some embodiments, the thermal cycling can be performed any number of times, such as any number greater than about 10 times, greater than about 20 times, greater than about 30 times, or from about 5 to about 80 times, about 10 to about 70 times, about 20 to about 60 times, or preferably from about 30 to about 50 times. In some other embodiments, the thermal cycling can be optimized for fast thermal cycling. Such protocols and apparatuses for fast thermal cycling can be found in, for example, U.S. Pat. No. 6,210,882, or Kopp, et al., *Science* 280:1046-1048 (1998); Chiou, et al., *Anal. Chem.* 73:2018-2021 (2001) (for modified electric heating elements); Kalinina, et al., *Nucleic Acids Res.* 25:1999-2004 (1997) (for hot air cyclers); and Giordano, et al., *Anal. Biochem.* 291:124-132 (2001) (for infrared controlled reactions), the disclosures of which are fully incorporated herein by reference in their entireties.

Such PCR thermal cycling can be performed on a variety of instruments known to those of skill in the art. Some instruments can be commercially available, for example, from Applied Biosystems (e.g., AB SDS Instruments 7300 Real-Time PCR System, 7500 Real-Time PCR System, 7500 Fast Real-Time PCR System, 7900HT Real-Time PCR System, StepOne Real-Time PCR System and StepOne Plus Real-Time PCR System, or ViiA 7 Real-Time PCR System). It is to be understood that a wide variety of instruments are known in the art that may be useful in the present methods, including those not specifically disclosed herein.

In other embodiments, the present compositions can be used in methods for one-step (or coupled) RT-PCR. In some embodiments, RT-PCR reaction mixtures are incubated at a temperature sufficient to synthesize a DNA molecule complementary to all or portion of an RNA template (e.g., cDNA) and then incubated at a second temperature sufficient to amplify newly synthesized cDNA molecules. In accordance with the present methods, such temperatures used for cDNA synthesis can range from about 30° C. to about 75° C., about 35° C. to about 70° C., about 40° C. to about 60° C., or preferably from about 45° C. to about 55° C. In accordance with the present methods, such temperatures used for cDNA amplification can range from about 40° C. to about 80° C., about 45° C. to about 75° C., about 50° C. to about 70° C. or preferably from about 55° C. to about 65° C.

In some embodiments of the present methods (including, for example, those methods for nucleic acid synthesis, nucleic acid amplification or RT-PCR), the use of at least one PCR inhibitor blocking agent can increase tolerance to one or more PCR inhibitors. In some embodiments, increased tolerance can be indicated by, for example, a decrease in $C_t$ or increase in dRn (e.g., when analyzed by real time PCR) or by an increase in the amount of amplified product (e.g., when analyzed by agarose gel electrophoresis).

In some embodiments of the present methods, PCR inhibitor tolerance (as determined by $C_t$) can be increased by at least about 10% (e.g., about 10%, about 20%, about 30%, about 40%, about 60%, about 80%, etc.) when using at least one PCR inhibitor blocking agent compared to methods that do not. In other embodiments of the present methods, $C_t$ value is decreased at least one (e.g., at least 1, at least 2, at least 3 at least 5, at least 10, etc.) compared to the $C_t$ value achieved for methods that employ compositions without PCR inhibitor blocking agents. In other embodiments, methods that utilize compositions comprising at least 500 ng/µL BSA can decrease $C_t$ by at least 8 for reactions comprising at least 40 µM hematin, or by at least 7 for reactions comprising at least 10 ng/µL humic acid. In yet other embodiments, methods that utilize compositions comprising at least 1% fish gelatin decrease $C_t$ by at least 3 for reactions containing at least 10 ng/µL humic acid, or by at least 6 for reactions containing at least 0.06 U heparin.

Kits

In another embodiment, the present compositions and methods can be assembled into kits for use in reverse transcription or amplification of a nucleic acid molecule. Kits according to this embodiment can comprise a carrier means, such as a box, carton, tube or the like, having in close confinement therein one or more container means, such as vials, tubes, ampoules, plates, bottles and the like, wherein a first container means contains one or more polypeptides of the present teachings having reverse transcriptase activity and one or more DNA polymerases. When more than one reverse transcriptases or DNA polymerases are used, they can be in a single container as mixtures of two or more (e.g., 2, 3, 4, 5, etc) reverse transcriptases or DNA polymerases, or in separate containers. The kits provided herein can also comprise (in the same or separate containers), a suitable buffer, one or more nucleotides, one or more PCR inhibitor blocking agents, one or more probes or one or more primers. In some preferable embodiments, the reverse transcriptase(s), DNA polymerase(s), PCR inhibitor blocking agent(s), nucleotides and a suitable buffer are combined in a single tube or container.

In a specific embodiment, the reverse transcription and amplification kits can comprise one or more components (in mixtures or separately) including one or more polypeptides having reverse transcriptase activity and one or more DNA polymerases. Such reverse transcription and amplification kits can further comprise one or more nucleotides needed for synthesis of a nucleic acid molecule, one or more probes or one or more primers (e.g., oligo(dT) for reverse transcription). Preferred polypeptides having reverse transcriptase activity, DNA polymerases, nucleotides, probes, primers and other components suitable for use in the reverse transcription and amplification kits provided herein include those described above. The kits encompassed by this embodiment can further comprise additional reagents and compounds necessary for carrying out standard nucleic acid reverse transcription and/or amplification protocols. Such polypeptides having reverse transcriptase activity, DNA polymerases, PCR inhibitor blocking agents, nucleotides, probes, primers, and additional reagents, components or compounds can be contained in one or more containers, and can be contained in such containers in a mixture of two or more of the above-noted components or can be contained in the present kits in separate containers. Those of skill in the art will understand that other components, either in the same tube or in separate tubes, may also be included in the kit to further facilitate or enhance reverse transcription or amplification. Such components or additives, can include for example, $Mg^{2+}$, uracil DNA glycosylase, a passive reference control to minimize sample-to-sample or well-to-well variations in quantitative real-time DNA-detection assays (e.g., dyes such as ROX) and various hot start components (e.g., antibodies, oligonucleotides, beads, etc).

In another embodiment, the present kits can comprise compositions for use in nucleic acid synthesis (e.g., RT-PCR). Such compositions can be formulated as concentrated stock solutions (e.g., 2×, 3×, 4×, 5×, 6×, etc). In some embodiments, the compositions can be formulated as concentrated stock solutions in a single tube or container, comprising one or more polypeptides having reverse transcriptase activity and one or more DNA polymerases. In some preferred embodiments, such concentrated stock compositions can further comprise one more PCR inhibitor blocking agents, one or more nucleotides, one or more host start components, one or more passive reference controls, or one or more RNase inhibitor proteins (RIP) in a buffered solution. In some additional preferred embodiments, such buffer solutions can comprise glycerol, DMSO, $Mg^{2+}$, or a detergent (such as TWEEN 20 or NP-40). Collectively, the components of the present composition can be formulated together to create a master mix.

Typically master mixes for use in nucleic acid synthesis or amplification methods are stored at freezing temperatures to maintain enzyme stability (for example, of the reverse transcriptases or DNA polymerases) and are then thawed and diluted for subsequent assembly into final reactions mixtures. However, repeated master mix freeze-thaw cycles over time can lead to degradation of the enzymes resulting in decreased stability or functionality. In one aspect, the compositions, kits, or master mixes included in the kits described herein can be stored at about −16° C., about −18° C., about −20° C., about −22° C., about −24° C., about −26° C., about −28° C., about −30° C. without freezing. In some preferable embodiments, the compositions of the kits are stored at about −20° C. without freezing. In some embodiments, the present composition can be stored at freezing temperatures (e.g., below 0° C., below −5° C., below −20° C., below, −30° C., below −40° C., etc.) without having to be thawed prior to use. As used herein, the term "thaw," "thawing" or "thawed" refers to the process whereby heat changes something from a solid (e.g., frozen) to a gel or liquid. In some embodiments, the present compositions can be a liquid or a gel (or viscous liquid) at freezing temperatures. In some embodiments, such compositions, especially if in gel form, can be incubated at about 4° C. prior to subsequent use to ensure proper mixing, but do not require thawing per se.

Components of the kit other than the compositions disclosed herein can be provided in individual containers or in a single container, as appropriate. Instructions and protocols for using the kit advantageously can be provided.

It will be readily apparent to one of ordinary skill in the relevant arts that other suitable modifications and adaptations to the methods and applications described herein may be made without departing from the scope of the present disclosure or any embodiment thereof. All publications, patents, and patent applications mentioned in this specification are herein incorporated by reference to the same extent as if each individual publication, patent, or patent application was specifically and individually indicated to be incorporated by reference.

Described herein below are examples which are included herewith for purposes of illustration only and are not intended to be limiting of the present disclosure.

Example 1

An Exemplary Master Mix for Use in RT-PCR/PCR Reactions

An exemplary composition was formulated as a four-fold (4×) concentrated stock solution comprising 4 U/µL thermostable reverse transcriptase (e.g., M-MLV), 0.4 U/µL thermostable DNA polymerase (e.g., Taq), +/− PCR inhibitor blocking agents (as indicated below), nucleotides at 3.2 mM each (e.g., dTTP, dATP, dCTP, dGTP), 0.8 U/µL RNase Inhibitor Protein (RIP), 152 nM hot start component, 24% glycerol, 0.04% nonionic detergent, and 240 nM passive reference dye in a buffered salt solution. The exemplary master mix was tested in a number of assays as described in the following Examples below.

Example 2

The Effect of Fish Gelatin Concentration on PCR Inhibition by Humic Acid and Heparin RT-PCR (TaqMan Gene Expression Assays Hs00817723_g1 (ACADVL)) was performed using ing of UHR RNA (Stratagene, La Jolla, Calif.) in 1×20 µL reactions using the exemplary master mix described above. Assays were performed according to the manufacturer's instructions or with any changes indicated below, except that 0.5× of the assay was used per reaction. 10 ng/µL Humic acid (Fluka 53680) and 0.01 U to 0.1 U Heparin (Sigma H3393) were spiked in to separate RT-PCR reaction tubes in the presence of 0-1% fish gelatin. Water was used in place of an inhibitor in the control reactions. All combinations of fish gelatin and inhibitors were run in 4 technical replicates. RT-PCR was performed on a 7900HT Fast Real-Time PCR System (Life Technologies, Foster City, Calif.) using the following thermal conditions: 50° C. for 5 m, 95° C. for 20 s, (95° C. for 15 s, 60° C. for 60 s)×40 cycles. Each inhibitor/fish gelatin combination was evaluated based on $C_t$ value.

As shown in FIG. 1, RT-PCR reactions with 10 ng/μL were fully inhibited by humic acid when 0-0.6% fish gelatin was added to the reaction mixture. This was exhibited by a $C_t$ of 40 compared to a $C_t$ of approximately 30 observed in reactions without any inhibitors. However, increased humic acid tolerance (at 10 ng/μL) was observed when 0.8% and 1% fish gelatin was added to the reaction, as exhibited by $C_t$s of 35.99 and 31.90, respectively. With the exception of reactions comprising the highest heparin concentrations (0.08 U and higher), diminishing heparin inhibition with the addition of fish gelatin starting from as low as 0.2% (for 0.04 U heparin) was found.

Example 3

The Effect of BSA on Humic Acid, Hematin, and Heparin Inhibition

RT-PCR (TaqMan Gene Expression Assays Hs00817723_g1 (ACADVL) PN 4331182, Life Technologies, Foster City, Calif.) was performed using ing of UHR RNA (Stratagene, La Jolla, Calif.) in 1×20 uL reactions using the exemplary master mix described above. Assays were performed according to the manufacturer's instructions or with any changes indicated below, except that 0.5× of the assay was used per reaction. 10 ng/μL Humic acid (Fluka 53680), 40 μM Hematin (Sigma H3281), 0.01 U or 0.1 U Heparin (Sigma H3393) were spiked in to separate RT-PCR reactions with the addition of 0-8000 ng/μL BSA. Water was used in place of an inhibitor in the control reactions. All combinations of BSA and inhibitors were run in 4 technical replicates. RT-PCR was performed on a 7900HT Fast Real-Time PCR System (Life Technologies, Foster City, Calif.) at the following thermal conditions: 50° C. for 5 m, 95° C. for 20 s, (95° C. for 15 s, 60° C. for 60 s)×40 cycles. Each inhibitor/BSA combination was evaluated based on $C_t$ and dRn values.

Figure 2:
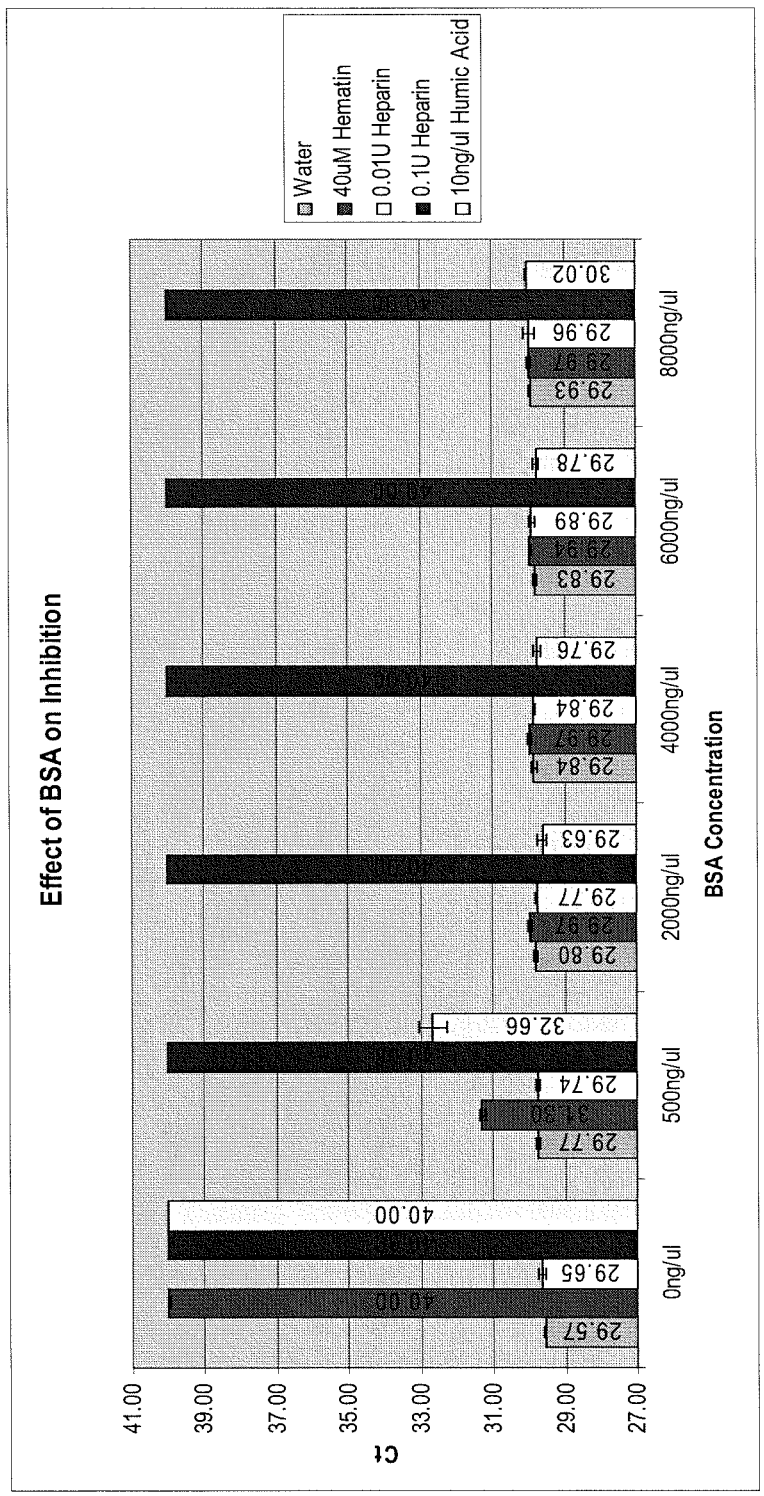
FIG. 2 depicts that BSA is effective in alleviating humic acid and hematin inhibition. At 2000 ng/μl BSA, inhibition by hematin and humic acid is completely eliminated, as reflected by comparable $C_t$ values to negative (water) controls.

As shown in FIG. 2, 0.01 U of heparin was observed not to be inhibitory to any of the RT-PCR reactions tested, as demonstrated by a comparable $C_t$ to that of the water controls. However, 0.1 U of heparin was observed to be completely inhibitory to the reactions for all concentrations of BSA tested. Inhibition was greatly reduced for hematin and humic acid with the addition of 500 ng/μL of BSA as exhibited by the $C_t$s going from 40, indicating complete inhibition, to 31.3 and 32.7 respectively. With the addition of 2000 ng/μL BSA, hematin and humic acid inhibition were completely eliminated, as demonstrated by $C_t$s of ~30 comparable to that of the water control.

Figure 3:
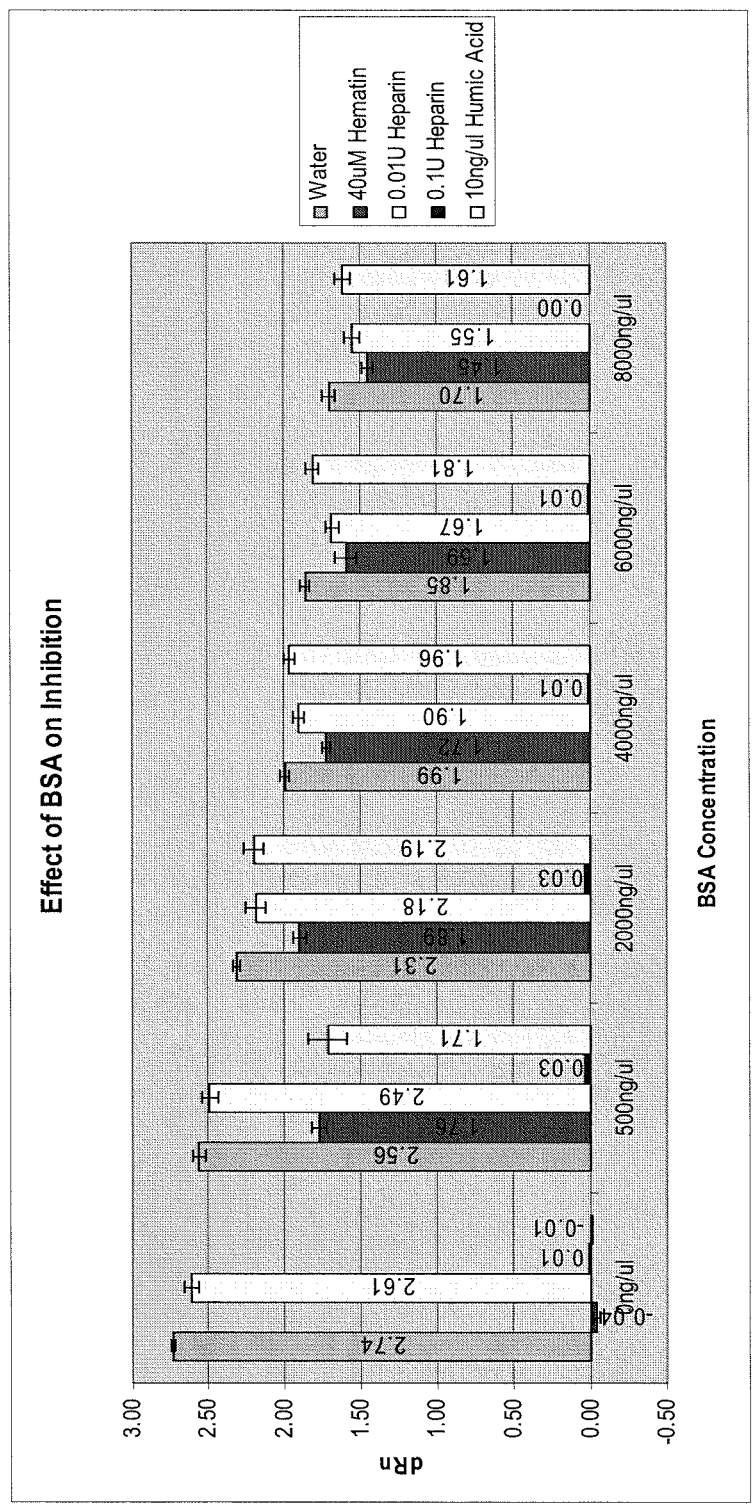
FIG. 3 depicts that dRn decreases with increasing amounts of BSA. Surprisingly, dRn values for control reactions also decrease with increasing BSA concentrations.
Figure 4:
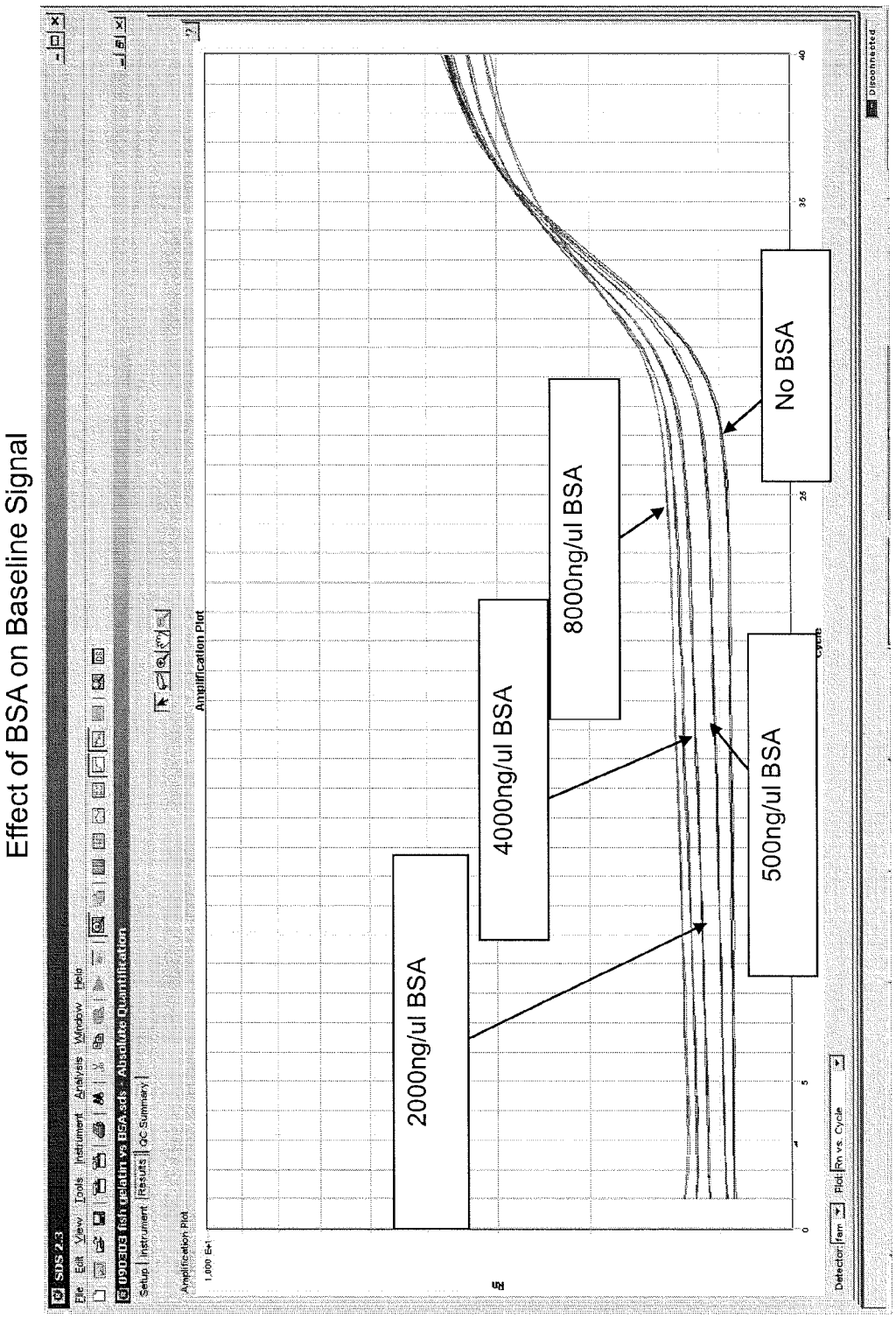
FIG. 4 depicts that baseline signal increases with increasing amounts of BSA.

As shown in FIG. 3, decreased dRn was also correlated to successful amplification. For hematin and humic acid, reactions comprising 2000 ng/μl BSA exhibited a higher dRn than reactions having only 500 ng/μL of BSA, indicating less inhibition with higher concentrations of BSA added. In comparison to the $C_t$ values for the water controls in FIG. 2, where the values were consistent for all concentrations of BSA added (indicating the absence of inhibition), dRn values decreased with increasing BSA concentration. As shown in FIG. 4, there was a correlation between the non-normalized raw signal and increasing baseline, as a result of increasing BSA concentrations.

Example 4

Determination of an Effective Concentration of Fish Gelatin as PCR Inhibitor Blocking Agent for Humic Acid, Hematin and Heparin RT-PCR (TaqMan Gene Expression Assay Hs00817723_g1 (ACADVL) PN 4331182, Life Technologies, Foster City, Calif.) was performed using ing of UHR RNA (Stratagene, La Jolla, Calif.) in 1×20 μL reactions using the exemplary master mix described above. Assays were performed according to the manufacturer's instructions or with any changes indicated below, except that 0.5× of the assay was used per reaction. 10 ng/μL Humic acid (Fluka 53680), 40 μM Hematin (Sigma H3281), 0.06 U and 0.08 U Heparin (Sigma H3393) were spiked in separate RT-PCR with the presence of 0-5% Fish Gelatin. Water was used in place of an inhibitor in the control reactions. All combinations of fish gelatin and inhibitors were run in 4 technical replicates. RT-PCR was performed on a 7900HT Fast Real-Time PCR System (Life Technologies, Foster City, Calif.) at the following thermal conditions: 50° C. for 5 m, 95° C. for 20 s, (95° C. for 15 s, 60° C. for 60 s)×40 cycles. Each inhibitor/fish gelatin combination was evaluated based on $C_t$ and dRn.

Figure 5:
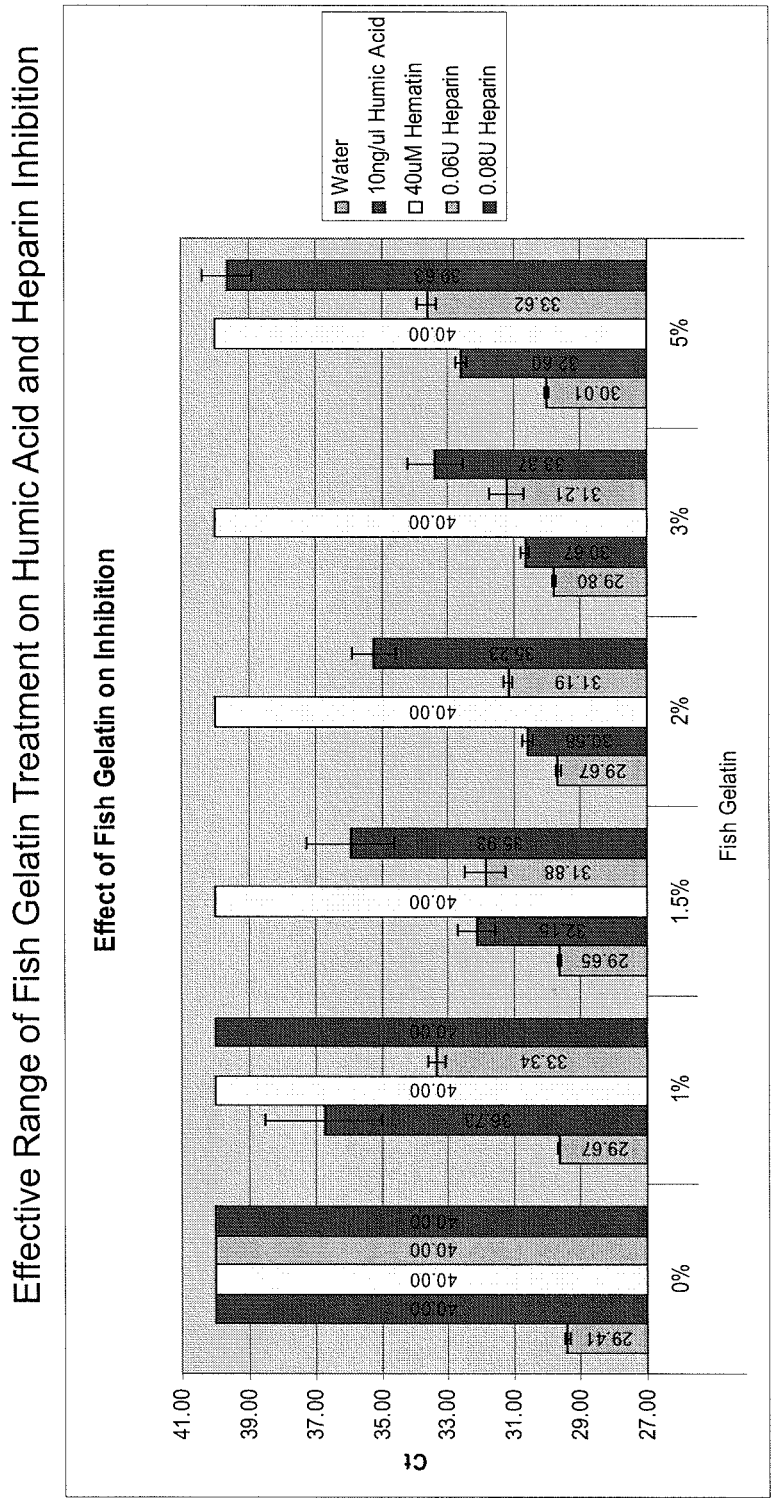
FIG. 5 depicts that fish gelatin is effective in alleviating humic acid and heparin inhibition (at the inhibitor concentrations tested) as indicated by lower $C_t$ values.

As shown in FIG. 5, reactions spiked with 10 ng/μL humic acid demonstrated a steady decrease in $C_t$ with increasing fish gelatin until at least about 2-3% fish gelatin, where $C_t$ values were the lowest at 30.6-30.7. The $C_t$ values increased slightly to 32.6 with the addition of 5% fish gelatin.

As shown in FIG. 5, the higher the concentration of heparin, the higher the concentration of fish gelatin was needed to counteract the inhibition. For example, amplification was observed with 1% fish gelatin when 0.06 U heparin was spiked in the reactions, while 1.5% fish gelatin was needed in order to observe amplification when 0.08 U heparin was spiked in the reactions. $C_t$ values were lowest at 31.2, with the addition of 2-3% fish gelatin for 0.06 U heparin, and lowest at 33.4, with the addition of 3% fish gelatin for 0.08 U heparin. Increased $C_t$ values were observed when fish gelatin concentrations were increased to 5% for both concentrations of heparin that were tested.

Figure 6:
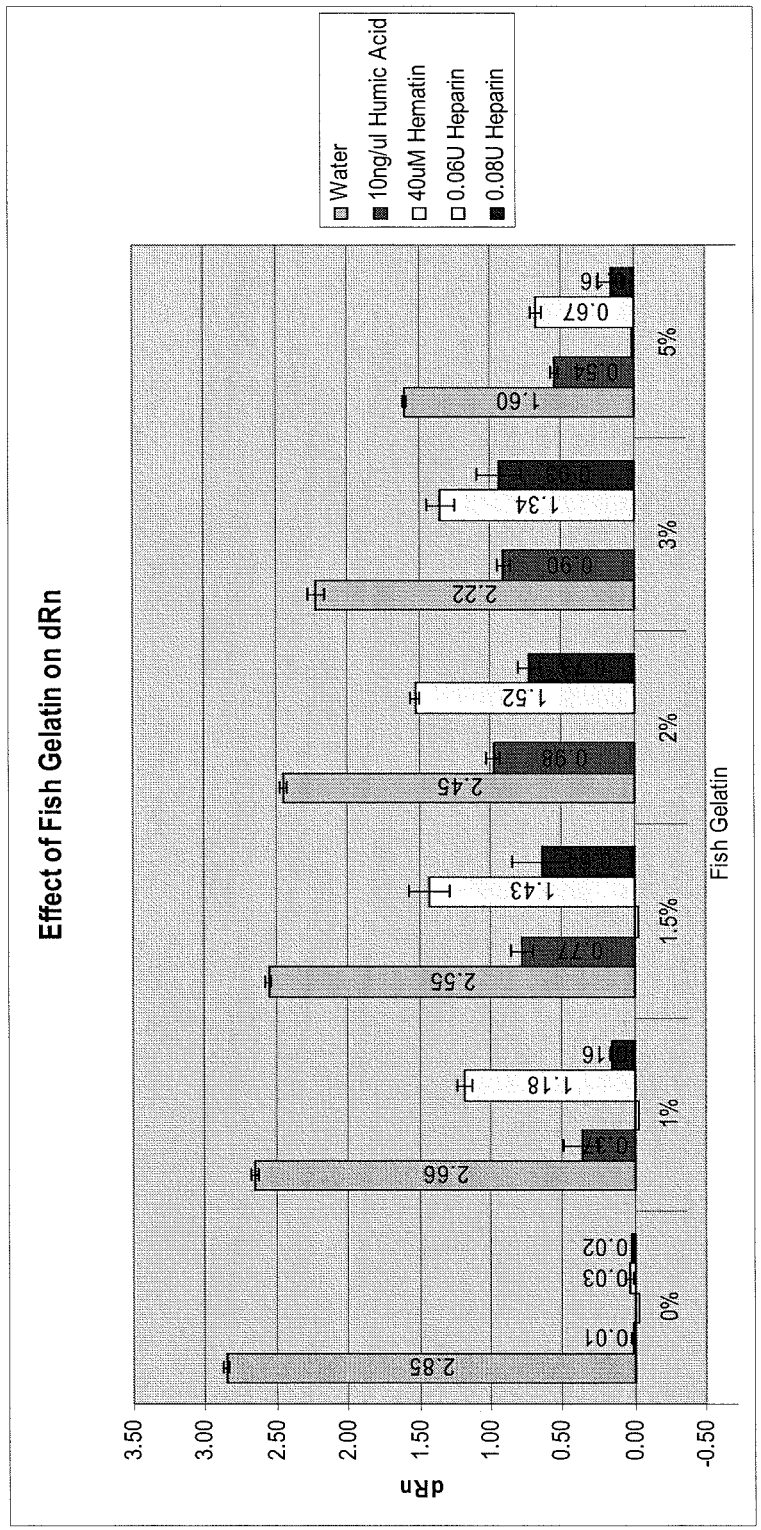
FIG. 6 depicts that dRn decreases gradually with increasing amounts of fish gelatin. Surprisingly, dRn values for control reactions also decrease with increasing fish gelatin concentrations.

Decreased PCR inhibition with increasing fish gelatin concentrations was observed as demonstrated by decreased $C_t$ values. As demonstrated in FIG. 6, this effect was corollary to increasing dRn values for all of the reactions comprising the various inhibitors tested. However, in the water control reactions (in the absence of any inhibitors), dRn values were also observed to decrease with increasing amounts of fish gelatin.

Example 5

The Effect of Fish Gelatin and BSA on Humic Acid, Hematin, and Heparin Inhibition RT-PCR (TaqMan Gene Expression Assay Hs00817723_g1 (ACADVL) PN 4331182, Life Technologies, Foster City, Calif.) was performed using ing of UHR RNA (Stratagene, La Jolla, Calif.) in 1×20 μL reactions using the exemplary master mix described above. Assays were performed according to the manufacturer's instructions or with any changes indicated below, except that 0.5× of the assay was used per reaction. 10 ng/μL Humic acid (Fluka 53680) and 40 μM Hematin (Sigma H3281) were spiked in separate RT-PCR reactions with a titration of 0-1% Fish Gelatin, 0-8000 ng/μL BSA, or a cross-titration of fish gelatin and BSA. Water was used in place of an inhibitor in control reactions. All combinations of fish gelatin/BSA and inhibitors were run in 4 technical replicates. RT-PCR was performed on a 7900HT Fast Real-Time PCR System (Life Technologies, Foster City, Calif.) at the following thermal conditions: 50° C. for 5 m, 95° C. for 20 s, (95° C. for 15 s, 60° C. for 60 s)×40 cycles. Each inhibitor/fish gelatin and/or BSA combination was evaluated based on $C_t$ and dRn values.

Figure 7:
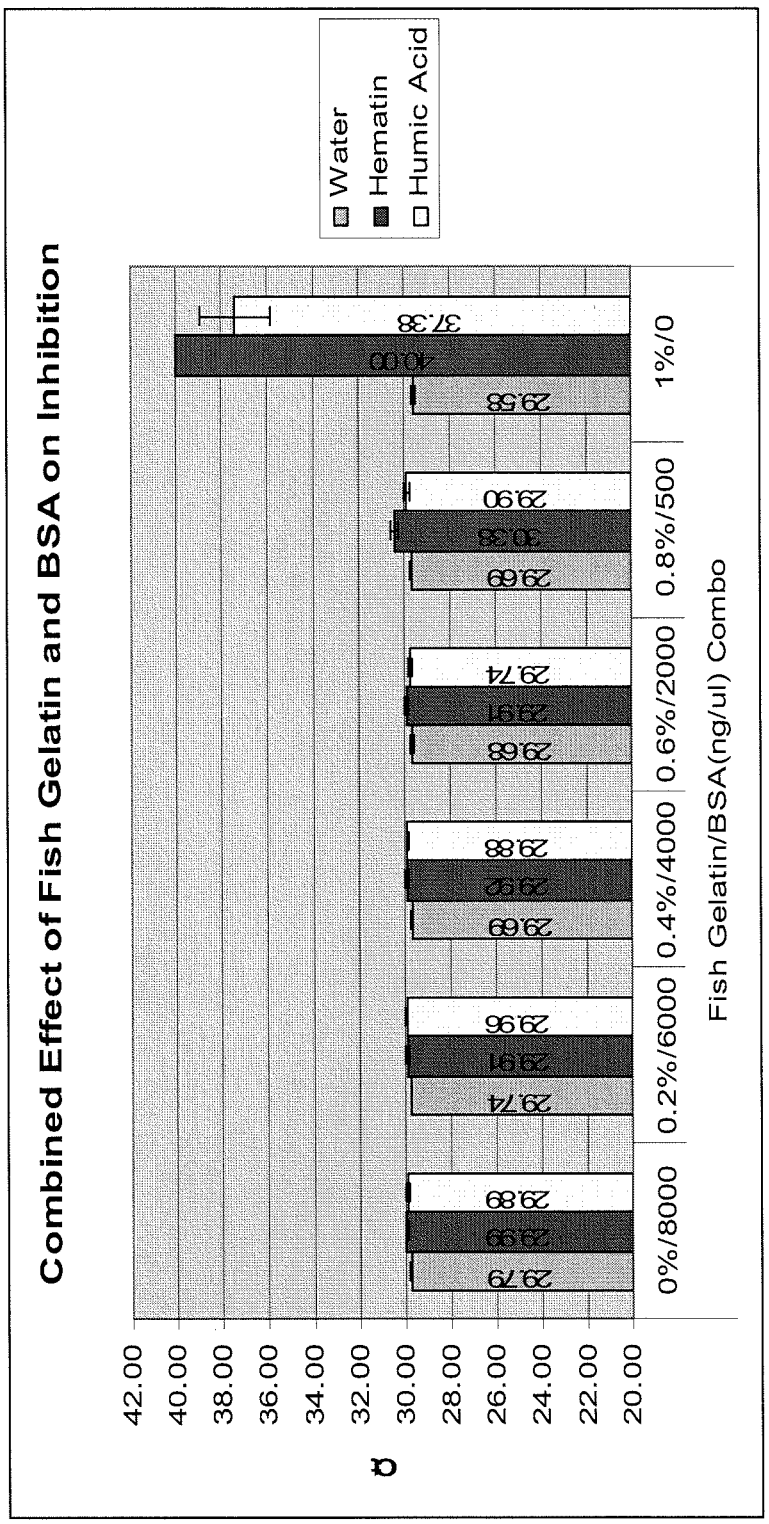
FIG. 7 depicts that the use of fish gelatin and BSA at lower concentrations, when used together, achieve comparable or better levels of inhibitor tolerance, as compared to reactions using either fish gelatin or BSA individually at higher concentrations. By way of non-limiting example, a combination of 0.8% fish gelatin and 500 ng/μl of BSA is more effective than using only 0.8% fish gelatin alone for humic acid inhibition or 500 ng/μL BSA alone for hematin and humic acid inhibition. By using less of each PCR inhibitor agent, when combined, the decrease in dRn and the shift in baseline signals are minimized.

FIG. 7 shows, that by using increasing amounts of fish gelatin combined with decreasing amounts of BSA, tolerance to hematin and humic acid increased when compared to the level of PCR inhibition for reactions comprising BSA alone. A combination of 0.8% fish gelatin and 500 ng/μL BSA almost completely eliminated hematin and humic acid inhibition, while 2000 ng/μL of BSA, alone, was needed for the same effect. All reactions comprising various combinations of both fish gelatin and BSA showed complete elimination of hematin and humic acid inhibition.

Example 6

The Effect of Fish Gelatin and BSA, Individually and in Combination, on Other PCR Inhibitors RT-PCR (TaqMan Gene Expression Assays Hs99999903_m1 (ACTB) PN 4331182, Life Technologies, Foster City, Calif.) was performed using 1 ng of UHR RNA (Stratagene, La Jolla, USA) in 1×20 μL reactions using the exemplary master mix described above. Assays were performed according to the manufacturer's instructions or with any changes indicated below, except that 0.5× of the assay was used per reaction. Various reaction tubes were prepared, comprising the following PCR blocking agents, in combination or alone: (1) no fish gelatin (FG) or BSA; (2) 0.5% FG only; (3) 800 ng/μl BSA only; (4) 0.5% FG+800 ng/ul BSA. The various reactions were then spiked with the following PCR inhibitors: (1) water (control); (2) 40 μM Hematin (Sigma H3281); (3) 0.04 U/rxn Heparin (Sigma H3393); (4) 10 ng/μL Humic acid (Fluka 53680); (5) 7.2 μg/rxn EDTA (Ambion AM9262); (6) 6.5 mM sodium citrate (two lots made from Sigma S4641); and (7) 0.825 μg/rxn Immunoglobin G (IgG) (Sigma 18640). Each reaction formulation was run in 4 technical replicates. RT-PCR was performed on a 7900HT Fast Real-Time PCR System (Life Technologies, Foster City, Calif.) at the following thermal conditions: 50° C. for 5 m, 95° C. for 20 s, (95° C. for 3 s, 60° C. for 30 s)×40 cycles. Results were evaluated based on $C_t$ values and the presence of amplicon product, as detected by gel electrophoresis using 4% agarose e-gels (Invitrogen, Carlsbad, Calif.).

Figure 8:
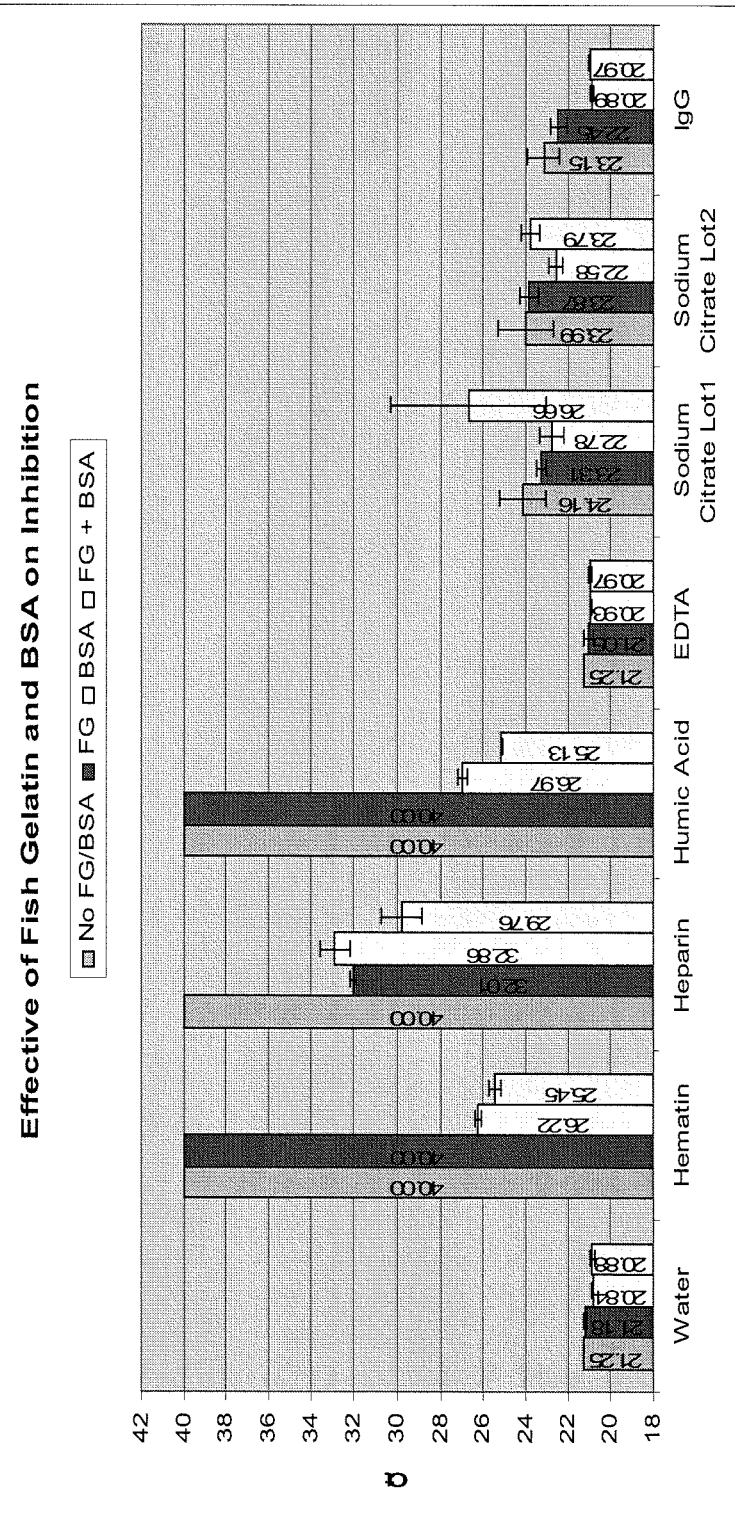
FIG. 8 depicts that fish gelatin and BSA, especially when combined, are effective in alleviating inhibition of various inhibitors, including hematin, heparin, humic acid, EDTA, sodium citrate, and immunoglobin G inhibition.

No FG or BSA:

As shown in FIG. 8, RT-PCR reactions were completely inhibited by hematin, heparin, and humic acid in the absence of any PCR inhibitor blocking agents, as exhibited by $C_t$ values of 40. For the particular reaction formulations tested, RT-PCR was partially inhibited by sodium citrate (both lot 1 and lot 2) and IgG, as exhibited by an increase in $C_t$ values of about 24 and 23 respectively, as compared to a $C_t$ value of about 21 in the case of the control reactions. In this particular experiment, EDTA (at 7.2 μg/rxn), did not appear to be inhibitory for any of the reaction conditions tested, and therefore was not evaluated further.

FG Only:

As shown in FIG. 8, RT-PCR reactions were completely inhibited by hematin and humic acid even in the presence of 0.5% fish gelatin. For all other inhibitors, a decrease in $C_t$ value was observed, when compared to the control reactions, indicating various degrees of tolerance to the different inhibitors by the addition of fish gelatin alone.

BSA Only:

As shown in FIG. 8, the presence of 800 ng/pL BSA partially relieved the inhibition of most of the inhibitors tested, and completely relieved the inhibition of IgG. BSA also appeared to be more effective than FG for all of the inhibitors tested, with the exception of heparin, as exhibited by the lower $C_t$ values of the reactions comprising BSA alone as compared to those comprising FG alone.

FG and BSA:

As shown in FIG. 8, reaction comprising a combination of FG and BSA conferred comparable tolerance to sodium citrate and IgG as those reactions comprising FG or BSA alone, as exhibited by the similar $C_t$ values for reactions with FG alone, BSA alone or FG+BSA. For the other inhibitors, the combination of FG and BSA was more effective than using FG or BSA alone. The lowest $C_t$ values were observed when using a combination of FG+BSA in the reactions as compared to all the other reaction formulations tested.

Figure 9:
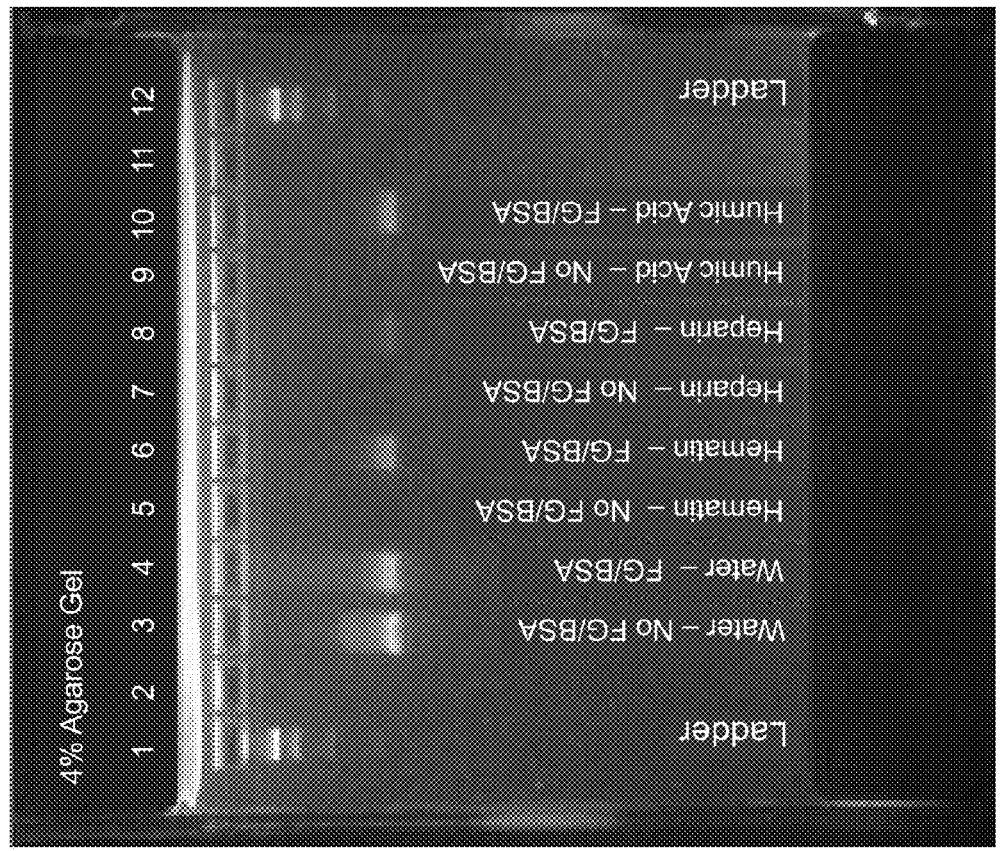
FIG. 9 depicts a photograph of an ethidium bromide-stained gel demonstrating that formulations comprising both fish gelatin and BSA can also be used to increase tolerance to various PCR inhibitors in PCR-based applications.

FIG. 9 further depicts the affect of FG and BSA, when used together, on hematin, heparin and humic acid inhibitors. As shown, in each example, the use of FG+BSA reduced the level of inhibition by these inhibitors on RT-PCR, as exhibited by the detection of amplified product by gel electrophoresis.

Example 7

The Feasibility of Using Master Mixes Comprising Both Reverse Transcriptase and Polymerase in a Single Reaction for Nucleic Acid Synthesis of DNA or RNA Templates Nucleic acid synthesis assays (TaqMan Gene Expression Assays Hs99999903_m1 (ACTB) PN 4331182, Life Technologies, Foster City, Calif.), Custom made RNA Virus assay (EV1) (see, Noble, et al., *Appl Environ Microbiol.* 72:1604-1612 (2006)), Custom made DNA Virus assay (ADV) (Jothikumar et al., *Applied and Enviromental Mircobiology*, 71:3131-3136 (2005)), Custom made RNA assay (BTV-PN 4415207, VetMax BTV Reagents, Life Technologies, Austin, Tex.), Custom made RNA assay (VLA-A) and Custom control assay (XenoIPC) were performed in 1×20 μL reactions using the exemplary master mix described above. Three non viral RNA target assays (ACTB, GPX4 and Xeno), four viral RNA target assays (EV1-Poliovirus, BTV-Blue Tongue Virus, VLA-A—InfluenzaA Virus) and one viral DNA target assay (ADV—Adenovirus) were analyzed at the various copy numbers or concentrations indicated in Table 1. Assays were performed according to the manufacturer's instructions (or with any other changes indicated herein), using the following assay concentrations:

ACTB: 0.5×;
EV1 [F/R/Pb]: 400 nM, 400 nM, 200 nM;
ADV [F/R/Pb]: 400 nM, 400 nM, 200 nM;
BTV: 1×;
VLA-A [F/R/Pb]: 400 nM, 400 nM, 200 nM; and
Xeno [F/R/Pb]: 400 nM, 400 nM, 200 nM The number of dilutions was dependent on the concentrations of stock template available. Assays were run using the following thermocycler conditions: 50° C. for 5 m, 95° C. for 20 s (95° C. for 3 s, 60° C. for 30 s)×40 cycles on 7900HT in 384 plate format.

Figure 10:
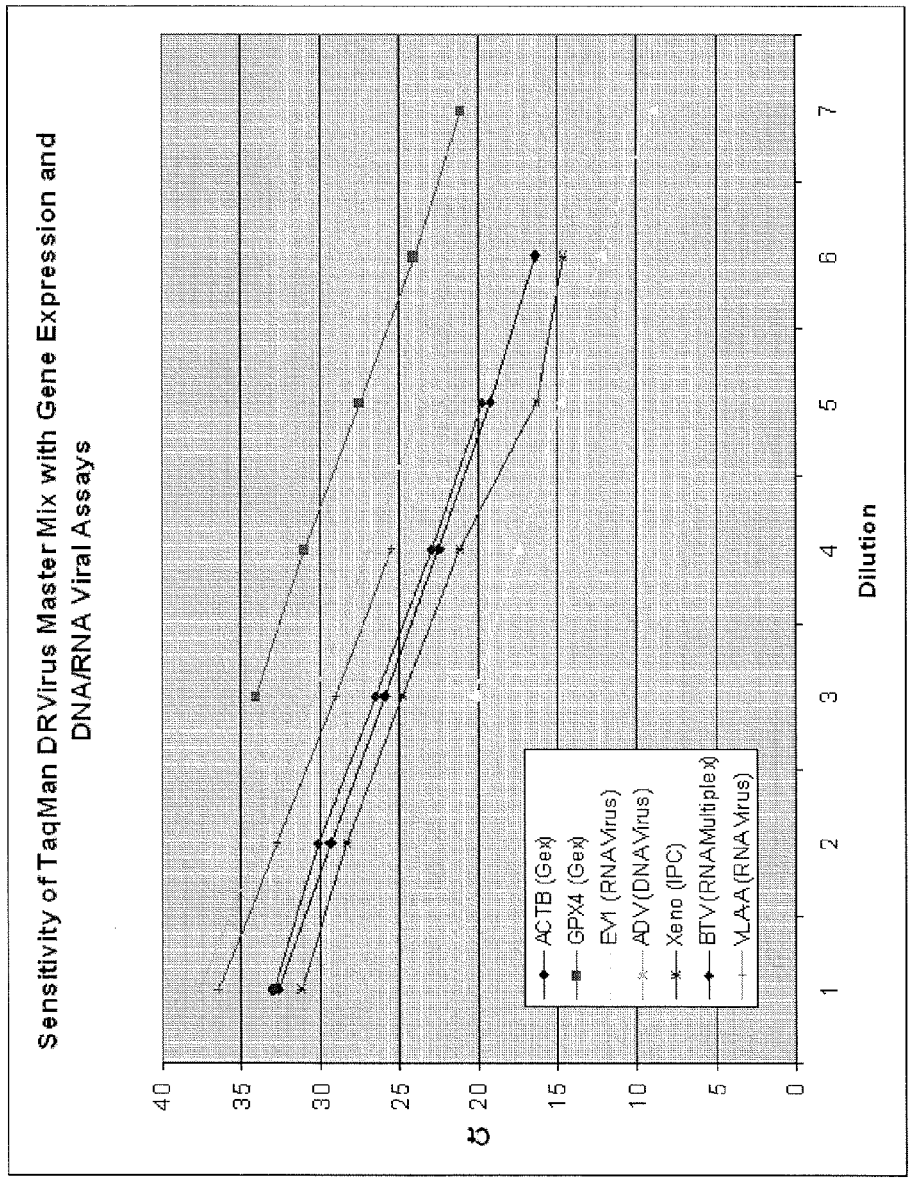
FIG. 10 depicts that one-step RT-PCR master mixes (i.e., compositions comprising both reverse transcriptase(s) and DNA polymerase(s) in a single reaction) provide comparable assay sensitivity when used for amplification of either DNA or RNA nucleic acid templates.

As shown in FIG. 10, consistent PCR efficiency (as depicted by linearity over different template input) was observed in all samples and assays tested, indicating reaction mixtures comprising both reverse transcriptase and polymerase are equally robust for amplification of RNA and DNA targets.

FIG. 10 shows that consistent PCR efficiency for ACTB was observed, as indicated by linearity across dilution points, from 0.0001 ng to 10 ng of RNA input per reaction; from 0.01 ng to 100 ng of RNA input per reaction for GPX4; from 0.01 ng to 100 ng of RNA input per reaction for EV1; from 0.0001× to 1× of DNA input per reaction for ADV; from 50 copies to 5,000,000 copies of RNA per reaction for Xeno; from 72 copies to 720,000 copies of RNA per reaction for BTV and from 10 copies to 10,000 copies of RNA per reaction for VLA.

TABLE 1

Concentrations/Copy Numbers of Various Nucleic Acid Templates Analyzed

|  | UHR (ng/rxn) | EV1 (ng/rxn) | BTV (copies/rxn) | VLA (copies/rxn) | ADV (X) | Xeno (copies/rxn) |
|---|---|---|---|---|---|---|
| Dilution 7 | 100 | 100 |  |  |  | 5.00E+07 |
| Dilution 6 | 10 | 10 |  |  |  | 5.00E+06 |
| Dilution 5 | 1 | 1 | 7.20E+05 |  | 1X | 5.00E+05 |
| Dilution 4 | 0.1 | 0.1 | 7.20E+04 | 10000 | 0.1X | 5.00E+04 |
| Dilution 3 | 0.01 | 0.01 | 7.20E+03 | 1000 | 0.01X | 5.00E+03 |
| Dilution 2 | 0.001 | 0.001 | 7.20E+02 | 100 | 0.001X | 5.00E+02 |
| Dilution 1 | 0.0001 | 0.0001 | 7.20E+01 | 10 | 0.0001X | 5.00E+01 |
| Example 8 |  |  |  |  |  |  |

Example 8

The Feasibility of Using Master Mixes Comprising Both Reverse Transcriptase and Polymerase in a Single Reaction for Multiplex Amplification RT-PCR assays (TaqMan NA and EU PRRSV Reagents, PN 4405547, and XenoRNA Controls, PN 4405548, Life Technologies, Austin, Tex.) were performed in 1×20 µL reactions using the exemplary master mix described above. Assays were performed according to the manufacturer's instructions or with any additional changes indicated below. The RNA virus target PRRSV (Porcine Reproductive and Respiratory Syndrome Virus) was analyzed in triplex. The assay included primers and probes for 2 targets labeled with FAM and VIC reporter dyes (NA and EU, respectively) and 1 exogenous IPC target labeled with NED reporter dye (Xeno). Seven dilutions (from 10 million copies to 10 copies per reaction) of the NA and EU templates were made by dilution with water. 1000 copies of Xeno IPC template were spiked into each reaction. RT-PCR was run at the following conditions: 50° C. for 5 m, 95° C. for 20 s (95° C. for 3 s, 60° C. for 30 s)×40 cycles on 7900HT in 384 format.

Figure 11:
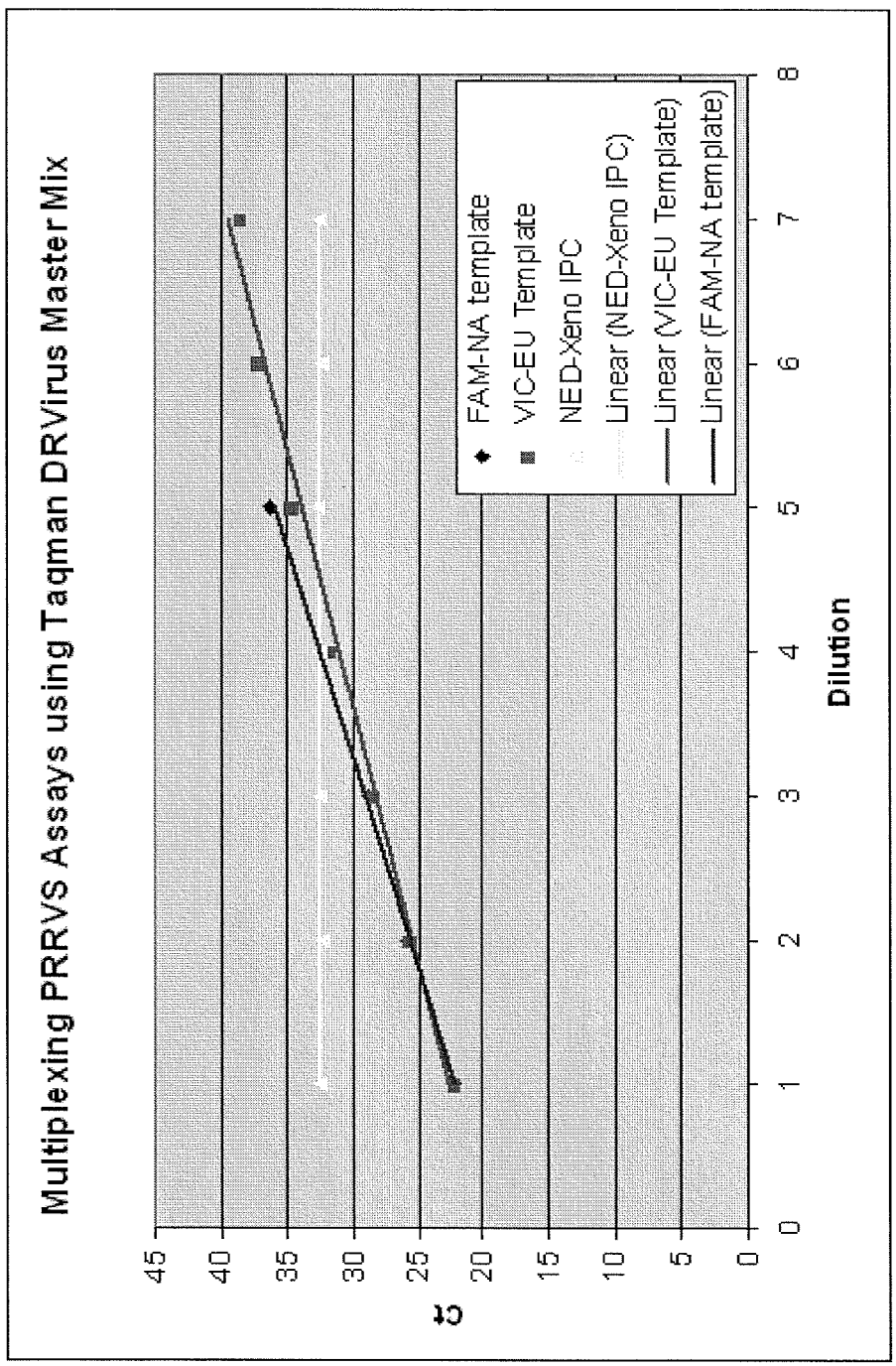
FIG. 11 depicts that one-step RT-PCR master mixes (i.e., comprising both reverse transcriptase(s) and DNA polymerase(s) in a single reaction) can be used for multiplex amplification assays.

As shown in FIG. 11, linear amplification was observed for two targets across different template input without affecting the consistency of exogenous IPC. Both NA and EU templates exhibited linear amplification from 10 million copies down to 1000 copies of template per reaction. No $C_t$ values were recorded with NA template at concentrations lower than 1000 copies/reaction. The standard deviation of Xeno $C_t$ values across the different target template concentrations was consistent having a standard deviation of only about 0.125 with an average $C_t$ value of 32.44.

Example 9

Detection of Viral Nucleic Acids

Human Papillomavirus (HPV), Epstein-Barr Virus (EBV), Hepatitis B and C Viruses (HBV and HCV) nucleic acid test controls were purified using conventional spin column methods and the purified samples were amplified in a dilution series using a 4× exemplary Master Mix, herein denoted "FVMM," to evaluate sensitivity, based on $C_q$ (which is equivalent to $C_t$, linearity and efficiency. Common PCR inhibitors including heparin, EDTA, hematin and humic acid, were spiked into the reactions to evaluate the tolerance of the system based on delta $C_q$ ($\Delta C_q$) between inhibitor-spiked samples and control samples.

All RT-PCR reactions were performed with 20 µL reaction volumes with the following thermal cycling profile: 50° C. for 5 m, 95° C. for 20 s (95° C. for 3 s, 60° C. for 30 s)×40 cycles. The sample reaction setup was as follows (all volumes are per one reaction):

| | |
|---|---|
| 4× MMix (FVMM) | 5 µL |
| 20× Target PPMix | 1 µL |
| Sample[†] | 5 µL |
| Water[‡] | 9 µL |
| Total Volume | 20 µL |

[†]Sample volume can be as much as the maximum volume allowed by the reaction (reaction volume (i.e., 20 µL) minus the sum of the volume of FVMM + PPMix.
[‡]Water volume is calculated to be the reaction volume minus the sum of the volume of all the other components (i.e., FVMM + PPMix + Sample).

Purified samples of HBV and HCV from nucleic acid test (NAT) controls and unpurified NAT controls of EBV and HPV were obtained from AcroMetrix (Benicia, Calif.). The unpurified EBV and HPV controls were purified using a conventional spin method with a sample input of 200 µL and an elution volume of 60 µL. Serial dilutions of the purified samples were then amplified. The limit of detection, PCR efficiency and linearity (R2) were evaluated. Assays were obtained from Applied Biosystems (Foster City, Calif.).

Amplification of the various nucleic acids were performed on the following instruments: Applied Biosystems 7900HT (HBV), Applied Biosystems 7500 Fast (HCV), and Applied Biosystems ViiA™ 7 (EBV and HPV). Table 2 shows the concentrations and copy numbers of each nucleic acid sample tested.

TABLE 2

Concentrations/Copy Numbers of Various Nucleic Acid Templates Analyzed

| Sample | HBV | | HCV | | EBV^ | | HPV | |
| --- | --- | --- | --- | --- | --- | --- | --- | --- |
| | IU/rxn | Avg. Cq | IU/rxn | Avg. Cq | Copy/rxn | Avg. Cq | Fold* | Avg. Cq |
| Dilution 1 | 492 | 27.62 | 644 | 27.45 | 5.9E+05 | 22.17 | Neat | 29.45 |
| Dilution 2 | 49.2 | 30.82 | 128.8 | 29.91 | 58833.3 | 25.42 | 1:10 | 32.74 |
| Dilution 3 | 4.92 | 34.07 | 25.76 | 32.40 | 5883.33 | 28.67 | 1:100 | 36.11 |
| Dilution 4 | 0.49 | 37.23 | 5.15 | 34.43 | 588.33 | 31.64 | | |
| Dilution 5 | | | 2.58 | 35.45 | 58.83 | 35.91 | | |
| Dilution 6 | | | 1.29 | 36.38 | 5.88 | 38.72 | | |
| PCR Efficiency | 1.050 | | 1.013 | | 0.989 | | 0.996 | |
| $R^2$ | 1.000 | | 0.999 | | 0.998 | | 1.000 | |

^Copy/rxn listed for EBV assumes 100% DNA recovery from purification. Dilution 5 was determined to be 10-25 copies/rxn by digital PCR. A conservative estimate of 10 copies/rxn was assumed to be the limit of detection for EBV.
*5 µL of sample was used per reaction. Actual copy number was unable to be determined by digital PCR due to variable copy number of the HPV template.

As shown in Table 2, the FVMM formulation exhibited about 100% PCR efficiency with R2 values of close to 1.

Unpurified NAT control of Adenovirus (ADV) Type 1 was obtained from ZeptoMetrix (Buffalo, N.Y.) and purified using a conventional spin column method with a sample input of 500 µL and elution volume of 50 µL. The purified sample was pre-screened for a dilution factor that would generate a $C_q$ of about 35 and different amounts of common PCR inhibitors were spiked into the reactions. The ADV assay sequences were obtained from the literature (Gu et al. *J. Clin. Microbiol.* 41:4636-4641 (2003), herein incorporated by reference in its entirety). The effect of inhibition was evaluated by calculating the $\Delta C_q$ between the inhibitor-spiked samples and water control samples. The same inhibitor test was also run with RNA internal positive control (IPC) samples targeting a $C_q$ of about 29 as a reference.

Figure 12:
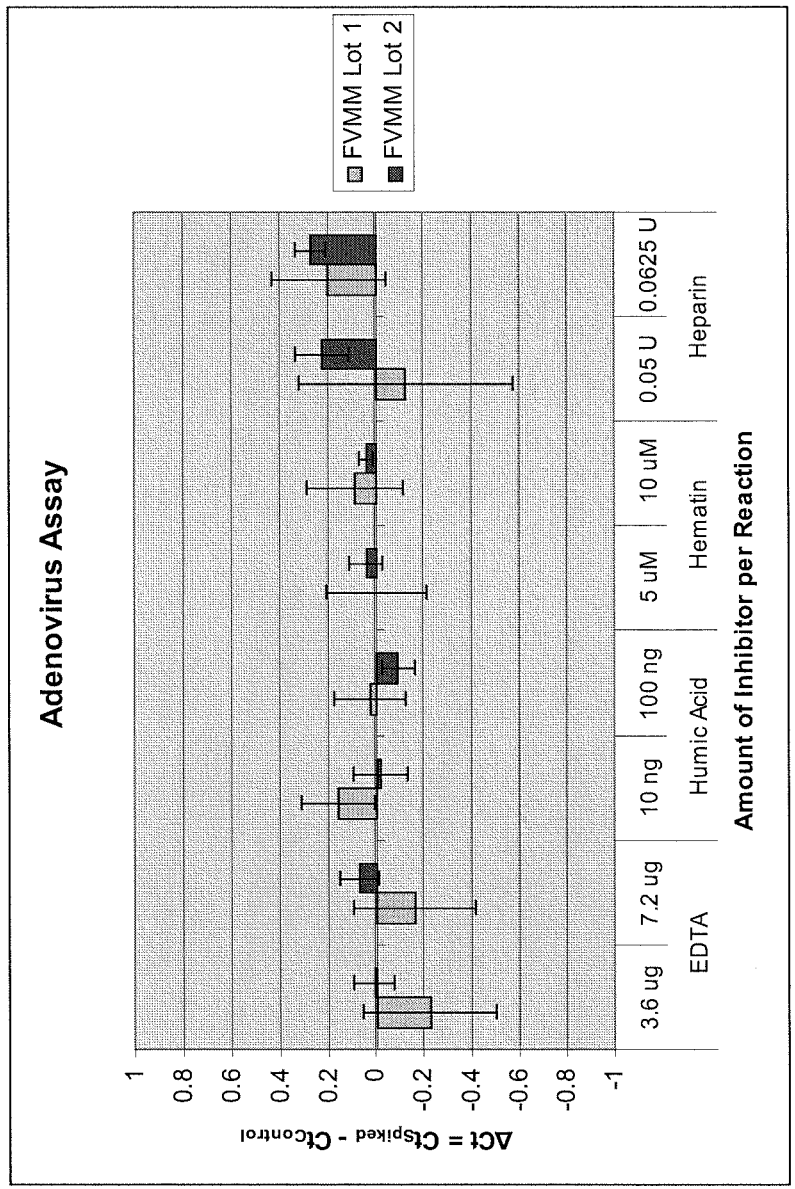
FIG. 12 depicts the effect of common PCR inhibitors on adenovirus amplification.

As shown in FIG. 12, four separate reaction setups of four technical replicates each were run for each inhibitor-concentration combination. $\Delta C_q$ was calculated as follows: $C_t$ of inhibitor-spiked reactions minus $C_t$ of water control reactions. The higher the $\Delta C_q$, the more the sample was inhibited. Though $\Delta C_q$ values were somewhat variable across the 16 replicates, they were all within $|1\ C_t|$, which suggests that there was no significant difference between spiked samples and the controls.

Figure 13:
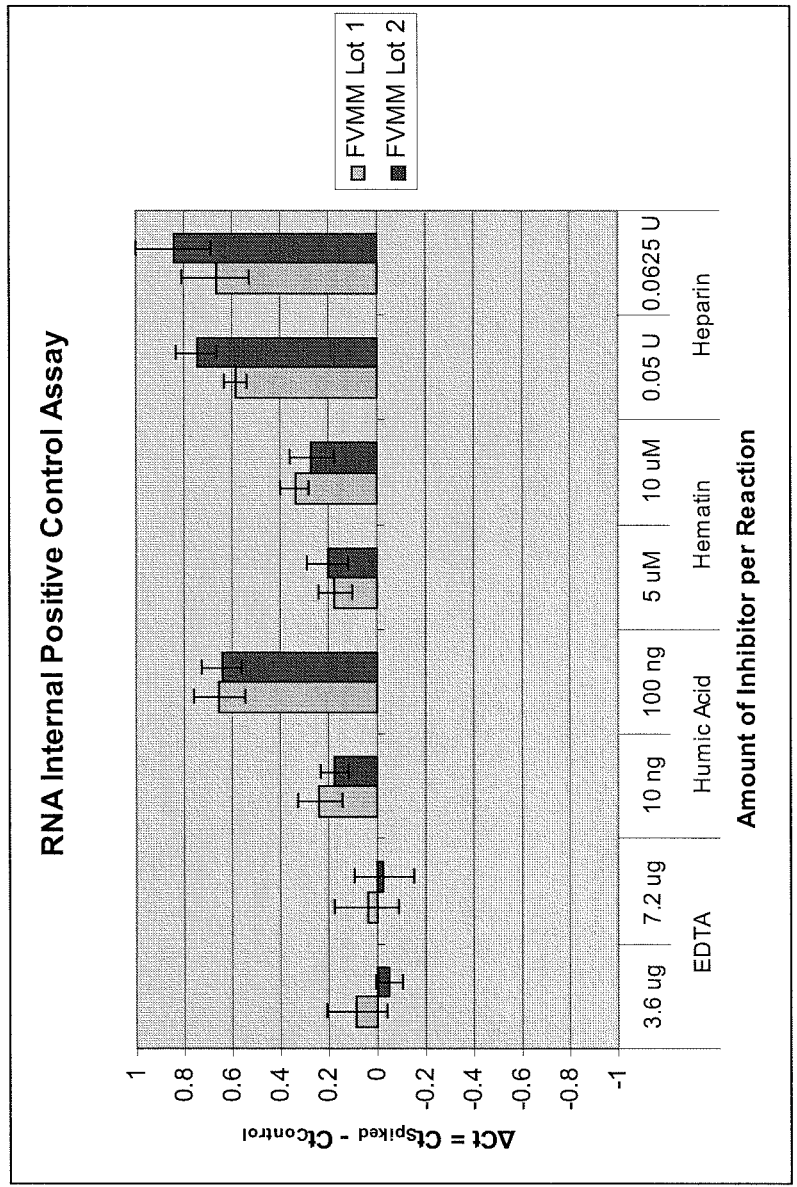
FIG. 13 depicts the effect of common PCR inhibitors on amplification of an RNA internal positive control (IPC) assay.

Using the same setup and evaluation as described for FIG. 12, the RNA IPC assays exhibited a higher sensitivity to inhibition than the ADV assay (see FIG. 13); however, the $\Delta C_q$s were still within $|1\ C_q|$, indicating that the FVMM formulation was tolerant of the four inhibitors at the concentrations tested.

Figure 14:
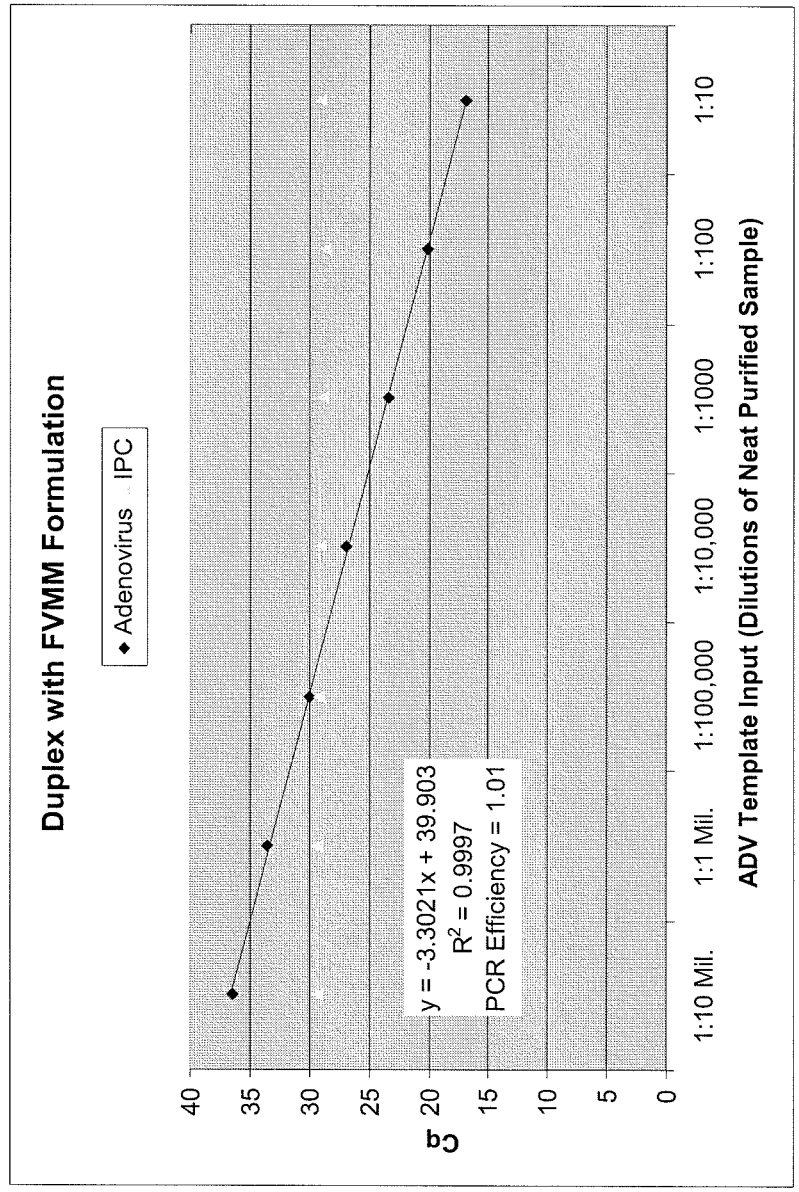
FIG. 14 depicts multiplex feasibility of the master mix in duplex amplification of adenovirus with IPC.

A serial dilution of the purified ADV DNA (see above) was amplified in a duplex reaction with the RNA IPC and the PCR efficiency and linearity (R2) were evaluated. As shown in FIG. 14, a 6-log dilution series of neat ADV DNA was duplexed with a constant input of RNA IPC template. Multiplexing did not affect the PCR efficiency or the linearity of the reactions.

The invention claimed is:

1. A method of performing RT-PCR of a nucleic acid sample comprising:
   mixing a composition comprising:
   at least one active reverse transcriptase;
   at least one active DNA polymerase; and
   a combination of PCR inhibitor blocking agents consisting essentially of 0.2% w/v-0.8% w/v fish gelatin and 500 ng/µl to 6000 ng/µl BSA configured to increase tolerance to one or more PCR inhibitors when present in the nucleic acid sample, with:
   a) a nucleic acid sample;
   b) one or more labeled probes;
   c) one or more primers; and
   performing a RT-PCR on the nucleic acid sample.

2. The method of claim 1, wherein the labeled probe is a TaqMan® probe.

3. The method of claim 1, wherein the one or more PCR inhibitors is selected from the group consisting of hematin, humic acid and heparin.

4. The method of claim 1, wherein the RT-PCR is performed in a single tube or reaction.

5. The method of claim 1, further comprising the step of removing the composition from storage at freezing temperatures prior to mixing with the nucleic acid sample, the one or more labeled probes and the one or more primers, wherein the composition does not require thawing.

6. The method of claim 1, wherein the increased tolerance is indicated by a decrease in $C_t$.

7. The method of claim 6, wherein the $C_t$ is decreased by at least one $C_t$.

8. The method of claim 1, wherein the tolerance is increased by at least 10% when compared to methods using compositions without the combination of PCR inhibitor blocking agents.

9. The method of claim 1, wherein the concentration of fish gelatin is 0.8% w/v to 4% w/v.

10. The method of claim 1, wherein the concentration of fish gelatin is 0.5% w/v.

11. A method for amplifying a nucleic acid molecule, the method comprising:
   mixing a nucleic acid template with a composition comprising one or more reverse transcriptases, one or more DNA polymerases, and a combination of PCR inhibitor blocking agents consisting essentially of 0.2% w/v-0.8% w/v fish gelatin and 500 ng/µl to 6000 ng/µl BSA, to form a reaction mixture, wherein each of the PCR inhibitor blocking agents is present at a concentration sufficient to reduce PCR inhibition by the PCR inhibitors when present; and
   incubating the reaction mixture under conditions sufficient to amplify a nucleic acid molecule complementary to all or a portion of the nucleic acid template.

12. The method of claim 11, wherein the nucleic acid template is RNA.

13. The method of claim 12, wherein the combination of PCR inhibitor blocking agents increases tolerance to one or more PCR inhibitors and wherein the increase in tolerance is indicated by a decrease in $C_t$.

14. The method of claim 13, wherein the decrease in $C_t$ is by at least 1 $C_t$.

15. The method of claim 11, wherein the nucleic acid template is DNA.

16. The method of claim 11, wherein at least one of the PCR inhibitors is selected from the group consisting of hematin, humic acid or heparin.

17. The method of claim 11, wherein the concentration of fish gelatin is 0.4% w/v to 0.8% w/v.

18. The method of claim 17, wherein the concentration of fish gelatin is 0.4% w/v.

19. A method for nucleic acid synthesis, the method comprising:

mixing one or more first nucleic acid molecules with one or more polymerases, and a combination of PCR inhibitor blocking agents consisting essentially of 0.2% w/v-0.8% w/v fish gelatin and 500 ng/μl to 6000 ng/μl BSA; and incubating the mixture under conditions sufficient to make one or more second nucleic acid molecules complementary to all or a portion of the one or more first nucleic acid molecules.

20. The method of claim 19, wherein the one or more first nucleic acid molecules is RNA.

21. The method of claim 19, wherein the one or more first or second nucleic acid molecules is DNA.

22. The method of claim 19, wherein the step of mixing the one or more first nucleic acid molecules with one or more polymerases, and the combination of PCR inhibitor blocking agents further comprises one or more reverse transcriptases in the mixture.

23. The method of claim 19, wherein the concentration of fish gelatin is 0.4% w/v to 4% w/v.

24. The method of claim 23, wherein the concentration of fish gelatin is 0.5% w/v.

* * * * *